United States Patent
Kawamura

(10) Patent No.: US 8,383,411 B2
(45) Date of Patent: Feb. 26, 2013

(54) SPECIMEN PROCESSING SYSTEM AND SPECIMEN CONVEYANCE METHOD

(75) Inventor: Yoshiyuki Kawamura, Kobe (JP)

(73) Assignee: Sysmex Corporation, Kobe (JP)

( * ) Notice: Subject to any disclaimer, the term of this patent is extended or adjusted under 35 U.S.C. 154(b) by 333 days.

(21) Appl. No.: 12/587,931

(22) Filed: Oct. 14, 2009

(65) Prior Publication Data

US 2010/0093097 A1   Apr. 15, 2010

(30) Foreign Application Priority Data

Oct. 15, 2008   (JP) .................................. 2008-266232

(51) Int. Cl.
*G01N 35/02*   (2006.01)

(52) U.S. Cl. .......... 436/47; 422/536; 422/500; 422/501; 422/502; 436/180

(58) Field of Classification Search .............. 422/63–67, 422/50, 500–502, 536; 436/47, 180

See application file for complete search history.

(56) References Cited

U.S. PATENT DOCUMENTS

| | | | |
|---|---|---|---|
| 5,588,555 A | | 12/1996 | Kanamori et al. |
| 6,019,945 A | * | 2/2000 | Ohishi et al. ..................... 422/65 |
| 2002/0098596 A1 | * | 7/2002 | Matsubara et al. ........... 436/501 |
| 2005/0207938 A1 | * | 9/2005 | Hanawa et al. ................. 422/64 |

FOREIGN PATENT DOCUMENTS

| | | |
|---|---|---|
| JP | 10-282114 | 10/1998 |
| WO | WO2004/074845 A2 | 9/2004 |

* cited by examiner

*Primary Examiner* — Jyoti Nagpaul
(74) *Attorney, Agent, or Firm* — Brinks Hofer Gilson & Lione

(57) ABSTRACT

A specimen processing system comprising: a plurality of measurement units for acquiring a reagent from each of corresponding reagent containers, and performing measurement of a specimen for a common measurement item by using the reagent; a conveyance mechanism for conveying specimens to the measurement units; a reagent information acquirer for acquiring reagent information related to the reagent stored in each of the reagent containers; a conveying destination determiner for determining a conveying destination of specimens based on the reagent information acquired by the reagent information acquirer; and a conveyance controller for controlling the conveyance mechanism to convey specimens based on the conveying destination determined by the conveying destination determiner, is disclosed. Specimen conveyance method is also disclosed.

15 Claims, 23 Drawing Sheets

SPECIMEN PROCESSING SYSTEM AND SPECIMEN CONVEYANCE METHOD

RELATED APPLICATIONS

This application claims priority under 35 U.S.C. §119 to Japanese Patent Application No. 2008-266232 filed on Oct. 15, 2008, the entire content of which is hereby incorporated by reference.

FIELD OF THE INVENTION

The present invention relates to a specimen processing system and a specimen conveyance method for conveying a specimen to a plurality of measurement units for measuring a specimen.

BACKGROUND

Conventionally, a specimen processing system, including a plurality of specimen processing devices such as a specimen analyzer and a smear producing device, and a conveyance device for conveying specimens to supply to the specimen processing device, for conveying specimens to each specimen processing device by the conveyance device, and processing the conveyed specimens with the specimen processing device is known.

Japanese Laid-Open Patent Publication No. 10-282114 describes an automatic analyzer in which a main conveyance line for conveying specimen racks is arranged between a rack supplying section and a rack accommodating section and a plurality of analyzing units are arranged along the main conveyance line. In the automatic analyzer described in Japanese Laid-Open Patent Publication No. 10-282114, the specimen rack containing the specimen is placed on the main conveyance line from a sending port of the rack supplying section and conveyed towards the adapted analyzing unit by the conveying operation of the main conveyance line. A dispensing area is provided in correspondence to each analyzing unit, wherein the specimen on the specimen rack is dispensed to a reaction section of the analyzing unit in such dispense process area. The dispense processing area includes a reception port for receiving the specimen rack from the main conveyance line and a sending port for sending the specimen rack to the main conveyance line. Each conveyance path is defined by a combination of one of a plurality of sending ports and one of a plurality of reception port, so that a plurality of conveyance paths is formed as a whole. A control device for controlling the conveyance of the specimen rack selects the conveyance path adapted to the specimen rack positioned on one of the sending ports from a plurality of conveyance paths, and conveys the specimen rack towards the reception port of the selected conveyance path through the main conveyance line. Such conveyance is executed without the other specimen racks on the main conveyance line, wherein the specimen rack inserted the earliest is conveyed first if the specimen rack waiting to be conveyed is in plurals. The conveyance is also executed after checked that the reception port, which is the reception destination, can receive the specimen rack.

In such specimen processing system, the measurement unit cannot perform the measurement if the expiration date or the validity date of a reagent used for the measurement has expired or there is no reagent remaining. However, in the automatic analyzer described in Japanese Laid-Open Patent Publication No. 10-282114, the reagent cannot be efficiently used because the specimen rack is conveyed irrespective of the state of the reagent of each analyzing unit.

SUMMARY OF THE INVENTION

The scope of the present invention is defined solely by the appended claims, and is not affected to any degree by the statements within this summary.

A first aspect of the present invention is a specimen processing system comprising: a plurality of measurement units for acquiring a reagent from each of corresponding reagent containers, and performing measurement of a specimen for a common measurement item by using the reagent; a conveyance mechanism for conveying specimens to the measurement units; a reagent information acquirer for acquiring reagent information related to the reagent stored in each of the reagent containers; a conveying destination determiner for determining a conveying destination of specimens based on the reagent information acquired by the reagent information acquirer; and a conveyance controller for controlling the conveyance mechanism to convey specimens based on the conveying destination determined by the conveying destination determiner.

A second aspect of the present invention is a specimen processing system comprising: a plurality of measurement units for acquiring a reagent from each of corresponding reagent containers, and performing measurement of a specimen for a common measurement item by using the reagent; a conveyance mechanism for conveying specimens to the measurement units; a reagent information acquirer for acquiring reagent information related to the reagent stored in each of the reagent containers; a conveying destination determining means for determining a conveying destination of specimens based on the reagent information acquired by the reagent information acquirer; and a conveyance controller for controlling the conveyance mechanism to convey specimens based on the conveying destination determined by the conveying destination determining means.

A third aspect of the present invention is a specimen conveyance method by a specimen processing system including a plurality of measurement units for acquiring a reagent from each of corresponding reagent containers, and performing measurement of a specimen for a common measurement item by using the reagent, and a conveyance mechanism for conveying specimens to each of the measurement units; comprising: acquiring reagent information related to the reagent stored in each of the reagent containers; determining a conveying destination of specimens based on the acquired reagent information; and conveying specimens based on the determined conveying destination.

DETAILED DESCRIPTION OF THE PREFERRED EMBODIMENTS

The preferred embodiments of the present invention will be described hereinafter with reference to the drawings.

The present embodiment relates to a specimen processing system for acquiring reagent information of each measurement unit and conveying a specimen to the measurement unit based on the acquired reagent information.

[Configuration of Specimen Processing System]

Figure 1:
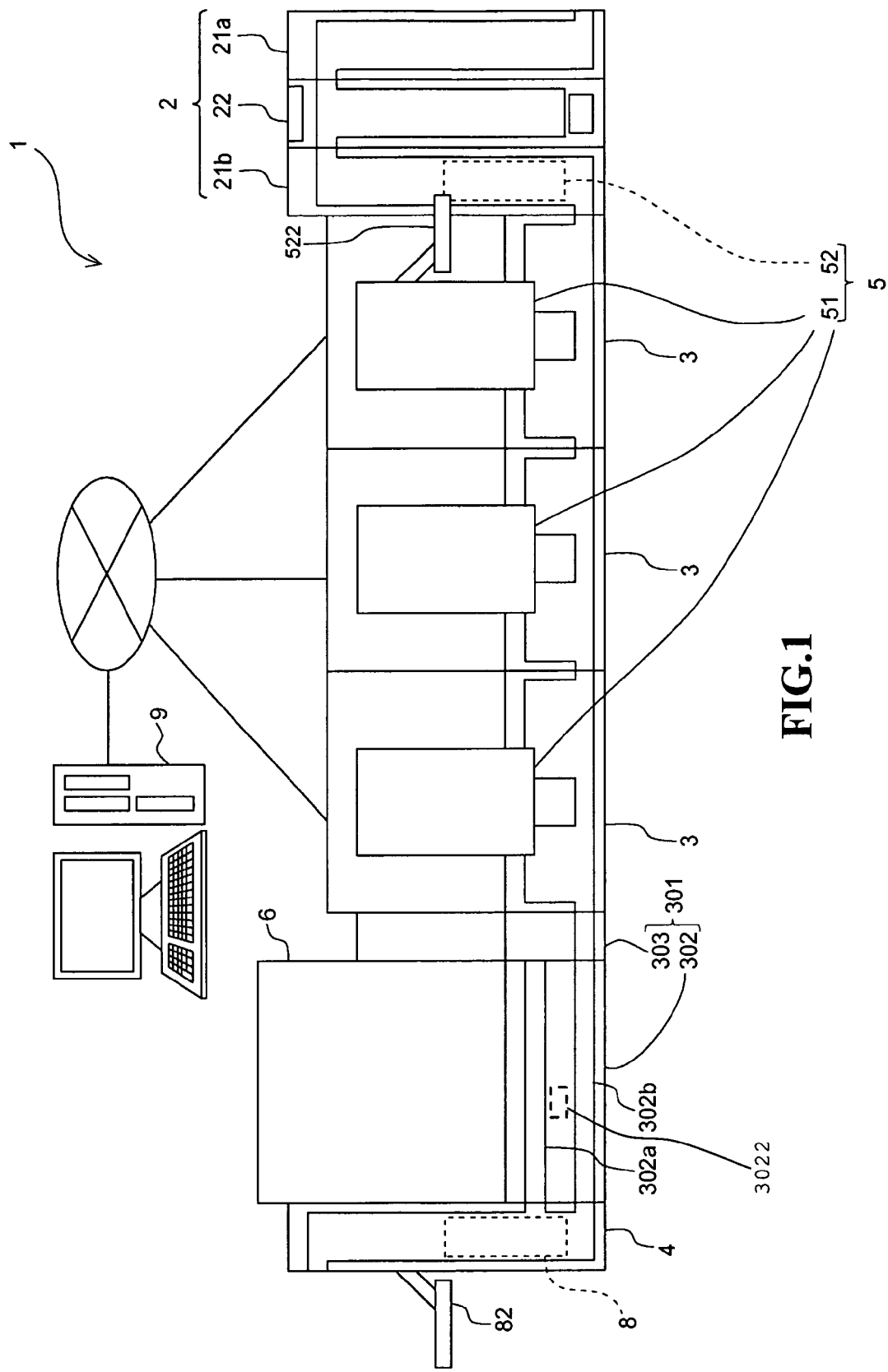
FIG. 1 is a schematic plan view showing an overall configuration of a specimen processing system according to an embodiment.

FIG. 1 is a schematic plan view showing an overall configuration of a specimen processing system according to the present embodiment. As shown in FIG. 1, the specimen processing system 1 is a system that executes processes such as measurement and smear production on a clinical specimen, and includes a specimen inserting device 2, specimen conveyance devices 3, 301, a specimen accommodating device 4, a blood cell analyzer 5, a smear producing device 6, and a system control device 8. The specimen processing system 1 according to the present embodiment is communicably connected to a host computer 9 by way of a communication network.

<Configuration of Specimen Inserting Device 2>

The specimen inserting device 2 includes two specimen sending units 21a, 21b, and a barcode reading unit 22 arranged between the two specimen sending units 21a, 21b. The specimen sending units 21a, 21b of the specimen inserting device 2 are configured to enable a sample rack accommodating a plurality of specimen containers to be mounted. The sample rack mounted on the specimen sending unit 21a is sent to the barcode reading unit 22 in order, wherein the barcode reading unit 22 reads the rack ID from a barcode of a barcode label attached to the sample rack and reads the specimen ID from the barcode of the barcode label attached to the specimen container. A controller of the specimen inserting device 2 is communicably connected to the system control device 8 through a LAN, and the rack ID and the specimen ID read in the above manner are transmitted to the system control device 8. The sample rack, which reading of the barcode is completed, is conveyed to the specimen sending unit 21b, and sent out from the specimen sending unit 21b to the specimen conveyance device 3.

Figure 2:
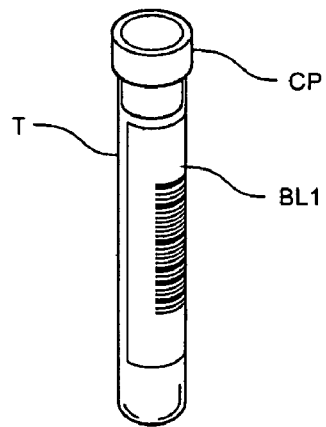
FIG. 2 is a perspective view showing an outer appearance of a specimen container.
Figure 3:
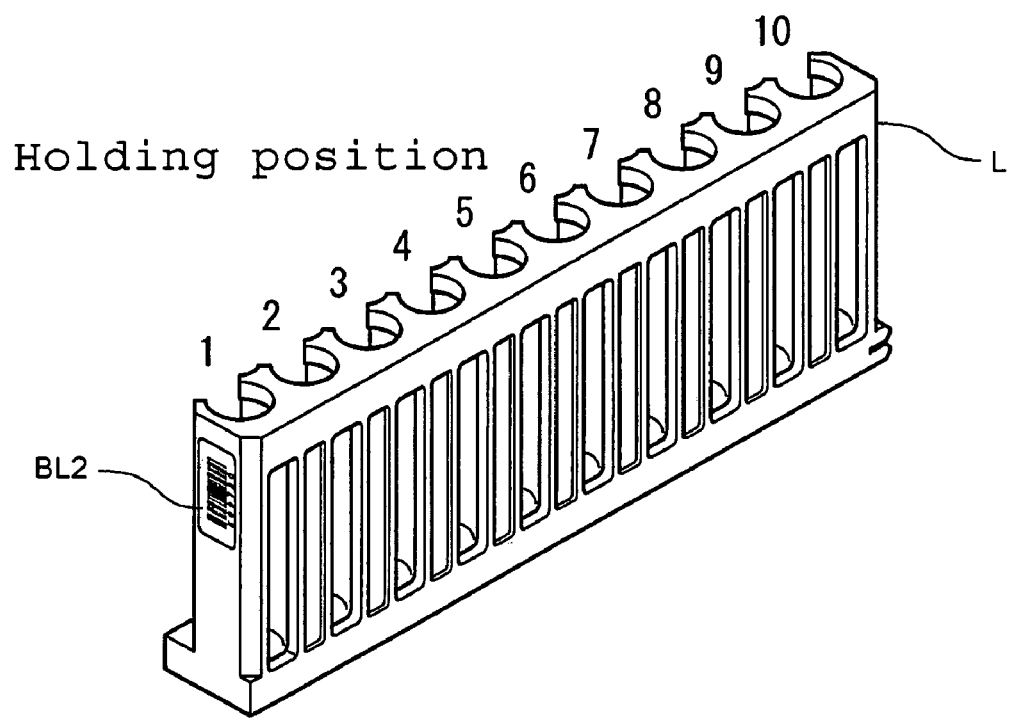
FIG. 3 is a perspective view showing an outer appearance of a sample rack.

FIG. 2 is a perspective view showing an outer appearance of the specimen container, and FIG. 3 is a perspective view showing an outer appearance of the sample rack. As shown in FIG. 2, the specimen container T has a tubular shape, and the upper end is opened. The blood specimen collected from a patient is accommodated therein, and the opening at the upper end is sealed by a lid C. The specimen container T is made of glass or synthetic resin having translucency, so that the blood specimen inside can be seen. A barcode label BL1 is attached to the side surface of the specimen container T. A barcode indicating the specimen ID is printed on the barcode label BL1. The sample rack L can hold ten specimen containers T side by side. Each specimen container T is held in a perpendicular state (standing state) in the sample rack L. A barcode label BL2 is attached to the side surface of the sample rack L. A barcode indicating the rack ID is printed on the barcode label BL2.

<Configuration of Specimen Conveyance Device 3>

The configuration of the specimen conveyance device 3 will now be described. As shown in FIG. 1, the specimen processing system 1 includes three specimen conveyance devices 3. The specimen conveyance devices 3, 3, 3 are arranged on the front side of three measurement units 51, 51, 51 of the blood cell analyzer 5. The adjacent specimen conveyance devices 3, 3 are connected, so that the sample rack L can be sent or received. The specimen conveyance device 3 on the rightmost side is connected to the specimen inserting device 2 described above so that the sample rack L conveyed out from the specimen inserting device 2 can be introduced. The specimen conveyance device 3 on the leftmost side is connected to the specimen conveyance device 301 so that the sample rack L can be conveyed out to the specimen conveyance device 301.

Figure 4:
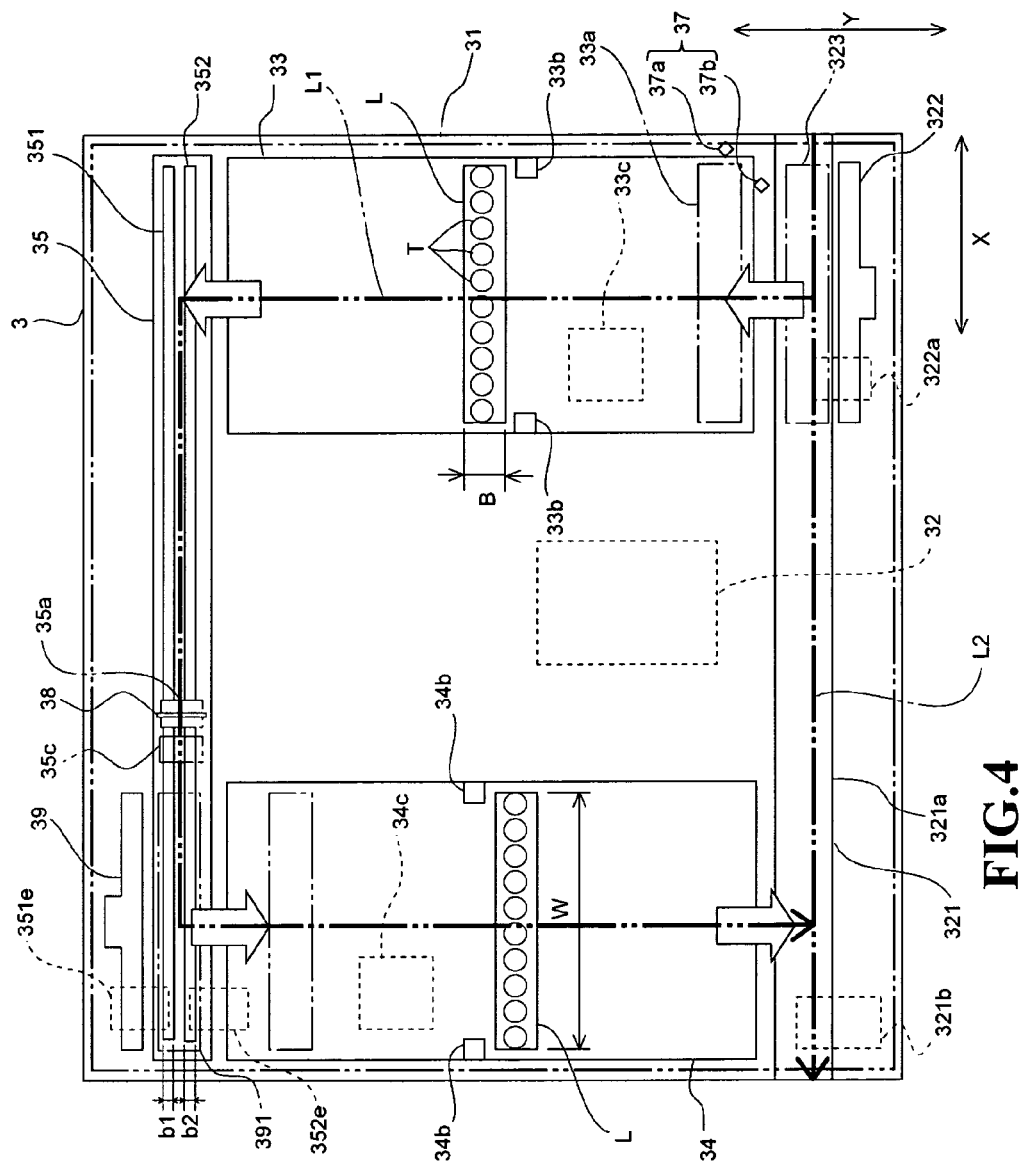
FIG. 4 is a plan view showing a configuration of a specimen conveyance device according to the embodiment.

FIG. 4 is a plan view showing a configuration of the specimen conveyance device 3. As shown in FIG. 4, the specimen conveyance device 3 includes a conveyance mechanism 31 for conveying the specimen, and a controller 32 for controlling the conveyance mechanism 31. The conveyance mechanism 31 includes a pre-analysis rack holder 33 capable of temporarily holding a plurality of sample racks L for holding the specimen container T accommodating the unanalyzed specimen, a post-analysis rack holder 34 capable of temporarily holding a plurality of sample racks L for holding the specimen container T from which the specimen is aspirated by the measurement unit 51, a rack conveyance portion 35 for horizontally and linearly moving the sample rack L in the direction of the arrow X in the figure to supply the specimen to the measurement unit 51 and conveying the sample rack L accepted from the pre-analysis rack holder 33 to the post-analysis rack holder 34, and a rack conveyance portion 321 for conveying in the sample rack L from a device on an upstream side of conveyance (specimen inserting device 2 or specimen conveyance device 3), and conveying out the sample rack L to a device on a downstream side of conveyance (specimen conveyance device 3 or specimen conveyance device 301) without supplying the specimen accommodated in the sample rack L to the measurement unit 51.

The pre-analysis rack holder 33 has a square shape in plan view, which width is slightly larger than the width of the sample rack L. The pre-analysis rack holder 33 is formed to be one step lower than the peripheral surface so that the sample rack L before the analysis is mounted on the upper surface. The pre-analysis rack holder 33 is connected to the rack conveyance portion 321, so that the sample rack L is sent from the rack conveyance portion 321 by the rack sending portion 322. The rack sensor 37 is attached near the pre-analysis rack holder 33, and a rack detection position 33a where the sample rack L is detected by the rack sensor 37 is provided on the pre-analysis rack holder 33. The rack sensor 37 is an optical sensor, and includes a light emitting portion 37a and a light receiving portion 37b. The light emitting portion 37a is arranged at the side of the rack detection position 33a, and the light receiving portion 37b is arranged on the front side of the rack detection position 33a. The light emitting portion 37a is arranged to emit light obliquely towards the front side, and the light receiving portion 37b is arranged to receive such light. Therefore, the sample rack L sent from the rack conveyance portion 321 is positioned at the rack detection position 33a, whereby the light emitted from the light emitting portion 37a is shielded by the sample rack L thereby lowering the light receiving level of the light receiving portion 37b, so that the sample rack L is detected by the rack sensor 37. A rack sending portion 33b is arranged towards the inner side in a projecting manner from both side surfaces of the pre-analysis rack holder 33. When the sample rack L is detected by the rack sensor 37, the rack sending portion 33b engages with the sample rack L due to its projection, and the sample rack L is moved towards the back when the rack sending portion 33b is moved towards the back side in such state (direction of approaching the rack conveyance unit 35). Such rack sending portion 33b is configured to be drivable by a stepping motor 33c arranged on the lower side of the pre-analysis rack holder 33.

As shown in FIG. 4, the rack conveyance unit 35 can move the sample rack L moved by the pre-analysis rack holder 33 in the X direction. A specimen container detection position 35a where the specimen container is detected by the specimen container sensor 38, and a specimen supply position 35c where the specimen is supplied to the measurement unit 51 of the blood cell analyzer 5 are provided on a conveyance path of the sample rack L by the rack conveyance portion 35. The rack conveyance portion 35 is configured to convey the sample rack L such that the specimen is conveyed to the specimen supply position 35c through the specimen container detection position 35a. The specimen supply position 35c is a position on the downstream side in the conveying direction by one specimen from the specimen container detection position 35a, wherein when the specimen is conveyed to the specimen supply position 35c by the rack conveyance unit 35, a hand portion of the measurement unit 51 of the blood cell analyzer 5, to be hereinafter described, grips the specimen container T of the relevant specimen to take out the specimen container T from the sample rack L, and the specimen is aspirated from the specimen container T to supply the specimen to the measurement unit 51. After conveying the specimen container to the specimen supply position 35c, the rack conveyance unit 35 waits for the conveyance of the sample rack L while the supply of the specimen is completed and the specimen container T is returned to the sample rack L.

Figure 5:
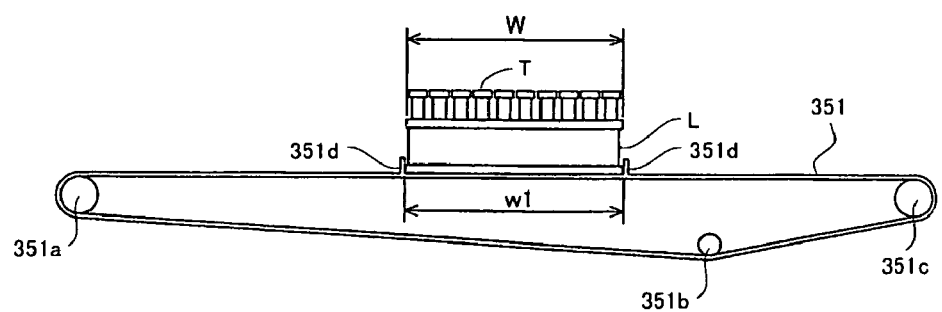
FIG. 5 is a front view showing a configuration of a first belt of a conveyance mechanism.
Figure 6:
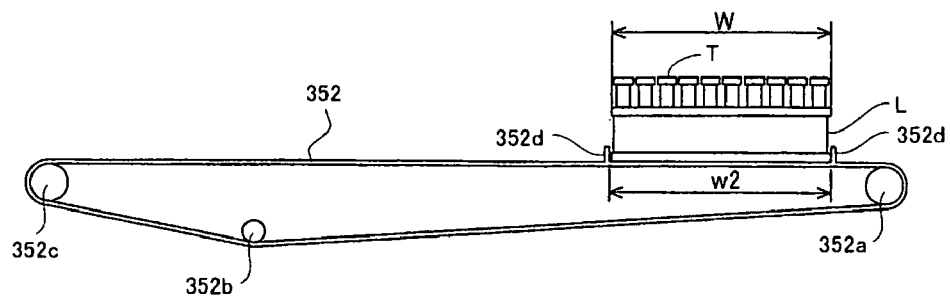
FIG. 6 is a front view showing a configuration of a second belt of the conveyance mechanism.

The rack conveyance unit 35 includes two belts, first belt 351 and a second belt 352, that are independently operable. The widths b1 and b2 in the direction of the arrow Y of the first belt 351 and the second belt 352 are the size of smaller than or equal to half of the width B in the direction of the arrow Y of the sample rack L. Such first belt 351 and second belt 352 are arranged in parallel so as not to run out from the width B of the sample rack L when the rack conveyance unit 35 conveys the sample rack L. FIG. 5 is a front view showing a configuration of the first belt 351, and FIG. 6 is a front view showing a configuration of the second belt 352. As shown in FIGS. 5 and 6, the first belt 351 and the second belt 352 are respectively formed to an annular shape, wherein the first belt 351 is arranged to surround rollers 351a to 351c, and the second belt 352 is arranged to surround rollers 352a to 352c. Two projecting pieces 351d having an inner width w1 slightly (e.g., 1 mm) larger than the width W in the X direction of the sample rack L are arranged on the outer peripheral part of the first belt 351, and similarly, two projecting pieces 352d having an inner width w2 of the same extent as the inner width w1 are arranged on the outer peripheral part of the second belt 352. The first belt 351 is configured to move the sample rack L in the direction of the arrow X by being moved at the outer periphery of the rollers 351a to 351c by the stepping motor 351e (see FIG. 4) while holding the sample rack L on the inner side of the two projecting pieces 351d. The second belt 352 is configured to move the sample rack L in the direction of the arrow X by being moved at the outer periphery of the rollers 352a to 352c by the stepping motor 352e (see FIG. 4) while holding the sample rack L on the inner side of the two projecting pieces 352d. The first belt 351 and the second belt 352 are also configured to move the sample rack L independent from each other.

The specimen container sensor 38 is a contact-type sensor, and includes a curtain-shaped contact piece, a light emitting element for emitting light, and a light receiving element (not shown). In the specimen container sensor, the contact piece is bent by contacting the detecting object of the detection target, and as a result, the light emitted from the light emitting element is reflected by the contact piece and received by the light receiving element. Therefore, when the specimen container T of the detection target accommodated in the sample rack L passes below the specimen container sensor 38, the contact piece is bent by the specimen container T, and the specimen container T can be detected.

The rack sending portion 39 is arranged to face the post-analysis rack holder 34, to be hereinafter described, with the rack conveyance unit 35 in between. The rack sending portion 39 is configured to horizontally and linearly move in the direction of the arrow Y by the driving force of the stepping motor 39a. Thus, when the sample rack L is conveyed to a position 391 (hereinafter referred to as "post-analysis rack sending position") between the post-analysis rack holder 34 and the rack sending portion 39, the sample rack L can be pushed and moved into the post-analysis rack holder 34 by moving the rack sending portion 39 towards the post-analysis rack holder 34 side. The sample rack L, which analysis is completed, is then sent from the rack conveyance unit 35 to the post-analysis rack holder 34.

The rack conveyance portion 321 extends in the direction of the arrow X in the figure, and can horizontally and linearly move the sample rack L in the direction of the arrow X. Such rack conveyance portion 321 includes an annular belt 321a and a stepping motor 321b, wherein the belt 321a rotates in the direction of the arrow X by the driving force of the stepping motor 321b. The sample rack L mounted on the belt 321a is thereby movable in the X direction. The rack sending portion 322 is arranged to face the pre-analysis rack holder 33 with the rack conveyance portion 321 in between on the front side of the pre-analysis rack holder 33. The rack sending portion 322 is configured to horizontally and linearly move in the direction of the arrow Y by the driving force of the stepping motor 322a. Thus, when the sample rack L is conveyed to a position 323 (hereinafter referred to as "pre-analysis rack sending position") between the pre-analysis rack holder 33 and the rack sending portion 322, the sample rack L can be pushed and moved into the rack detection position 33a in the pre-analysis rack holder 33 by moving the rack sending portion 322 towards the pre-analysis rack holder 33 side.

The post-analysis rack holder 34 has a square shape in plan view, which width is slightly larger than the width of the sample rack L. The post-analysis rack holder 34 is formed to be one step lower than the peripheral surface so that the sample rack L, which analysis is completed, is mounted on the upper surface thereof. The post-analysis rack holder 34 is connected to the rack conveyance unit 35, so that the sample rack L is sent from the rack conveyance unit 35 by the rack sending portion 39. A rack sending portion 34b is arranged towards the inner side in a projecting manner from both side surfaces of the post-analysis rack holder 34. When the sample rack L is conveyed in by the rack sending portion 39, the rack sending portion 34b engages with the sample rack L due to its projection, and the sample rack L is moved towards the front side when the rack sending portion 34b is moved towards the front side in such state (direction of approaching the rack conveyance portion 321). Such rack sending portion 34b is configured to be drivable by the stepping motor 34c arranged on the lower side of the post-analysis rack holder 34.

According to such configuration, the conveyance mechanism 31 is formed with a measurement line L1 being the conveyance line of the sample rack L passing through the specimen supply position 35c, and a skip line L2 being the conveyance line of conveying out the sample rack L that is conveyed in to the device on the downstream side without passing the specimen supply position 35c.

The conveyance mechanism 31 having such configuration is controlled by the controller 32. The controller 32 is configured by CPU, ROM, RAM, and the like, and the CPU can execute the control program of the conveyance mechanism 31 stored in the ROM. The controller 32 has an Ethernet (registered trademark) interface so as to be communicably connected to the information processing unit 52 and the system control device 8 through the LAN.

According to such configuration, the specimen conveyance device 3 conveys the sample rack L conveyed from the specimen inserting device 2 to the pre-analysis rack sending position 323 by the rack conveyance portion 321, moves the same to the pre-analysis rack holder 33 by the rack sending portion 322, sends the sample rack L from the pre-analysis rack holder 33 to the rack conveyance portion 35, and conveys the same by the rack conveyance portion 35, so that the specimen can be supplied to the measurement unit 51 of the blood cell analyzer 5. The sample rack L accommodating the specimen, which aspiration is completed, is moved to the post-analysis rack sending position 391 by the rack conveyance portion 35, and sent to the post-analysis rack holder 34 by the rack sending portion 39. The sample rack L held by the post-analysis rack holder 34 is moved to the rack conveyance portion 321, and conveyed out to the device of the post-stage (specimen conveyance device 3 or 301) by the rack conveyance portion 321. If the sample rack L accommodating the specimen to be processed in the measurement unit 51 or the smear producing device 6 at the downstream side in conveyance or the specimen, which analysis is completed, is accepted by the specimen conveyance device 3 from the device of the pre-stage, the sample rack L is conveyed out in the direction of the arrow X by the rack conveyance portion 321, and conveyed out as is to the specimen conveyance device 3 of the post-stage.

<Configuration of Specimen Conveyance Device 301>

As shown in FIG. 1, the specimen conveyance device 301 is arranged on the front side of the smear producing device 6. The specimen conveyance device 301 is connected, at the right side end, to the specimen conveyance device 3 positioned at the most downstream side in conveyance (left side in the figure) of the three specimen conveyance devices 3, 3, 3, and is connected, at the left side end, to the specimen accommodating device 4.

The specimen conveyance device 301 includes a conveyor 302 and a rack slider 303. The conveyor 302 is arranged with two rack conveyance paths 302a, 302b respectively extending in the left and right direction. The rack conveyance path 302a proximate to the smear producing device 6 is the measurement line for conveying the sample rack L accommodating the specimen to be supplied to the smear producing device 6. The rack conveyance path 302b distant from the smear producing device 6 is the skip line for conveying the sample rack L not accommodating the specimen to be supplied to the smear producing device 6. The conveyor 302 includes a controller 3022 for controlling each operation mechanism. The controller 3022 is configured by CPU, ROM, and RAM.

The rack slider 303 is arranged on the right side of the conveyor 302, and allocates and inserts the sample rack L to the measurement line 302a and the skip line 302b of the conveyor 302.

<Configuration of Specimen Accommodating Device 4>

The specimen accommodating device 4 is configured so that a plurality of sample racks L can be mounted. The specimen accommodating device 4 receives the sample rack L, which analysis and smear production are completed, from the specimen conveyance device 301, and accommodates the same.

<Configuration of Blood Cell Analyzer 5>

The blood cell analyzer 5 is a multi-item blood cell analyzer of optical flow cytometry method, and acquires the lateral scattered light intensity, the fluorescence intensity, and the like related to the blood cell contained in the blood specimen, categorizes the blood cell contained in the specimen based on the same, counts the number of blood cells for every type, creates a scattergram in which the categorized blood cells are colored by type, and displays the same. The blood cell analyzer 5 includes the measurement unit 51 for measuring the blood specimen, and the information processing unit 52 for processing the measurement data output from the measurement unit 51 and displaying the analysis result of the blood specimen.

As shown in FIG. 1, the blood analyzer 5 includes three measurement units 51, 51, 51 and one information processing unit 52. The information processing unit 52 is communicably connected to the three measurement units 51, 51, 51 and controls the operation of the three measurement units 51, 51, 51. The information processing unit 52 is also communicably connected to three specimen conveyance devices 3, 3, 3 arranged on the front side of the three measurement units 51, 51, 51.

Figure 7:
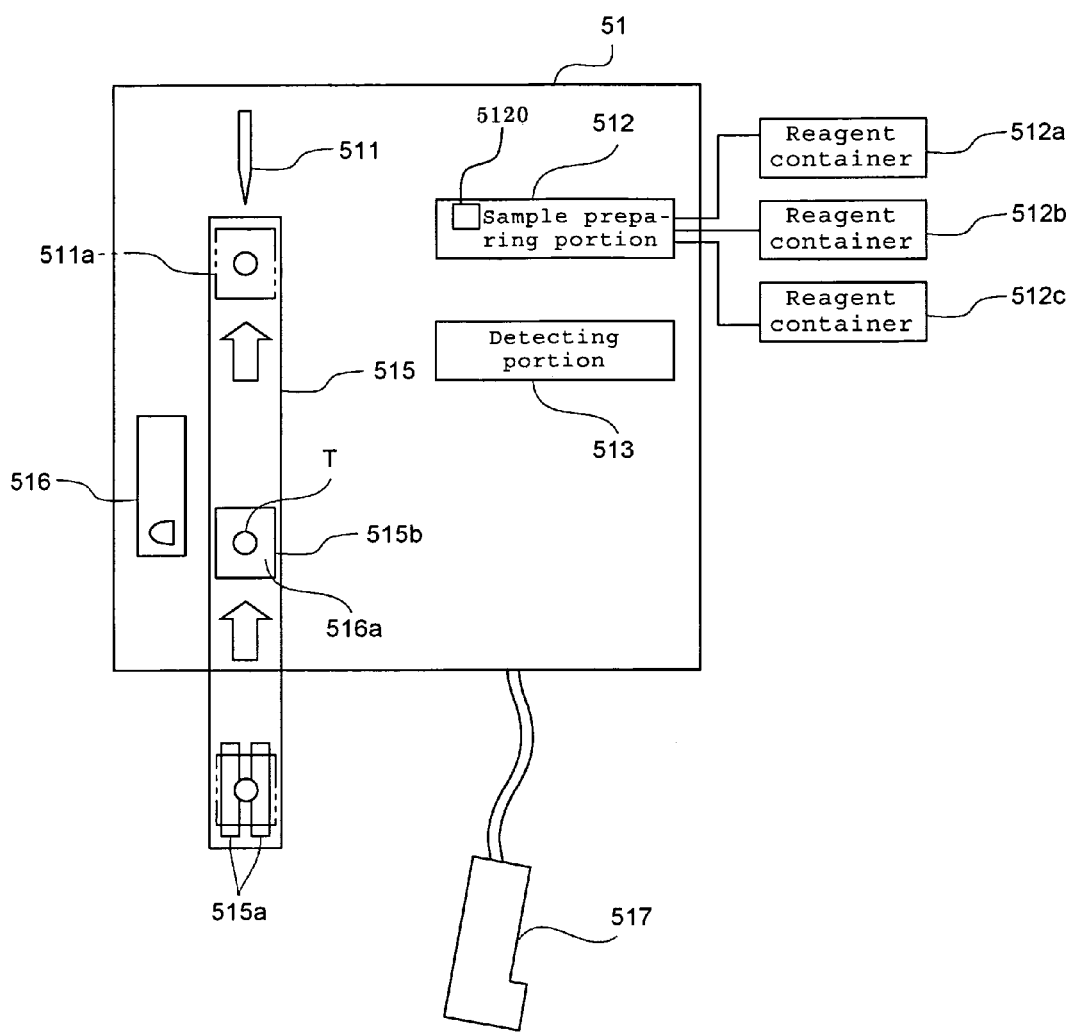
FIG. 7 is a block diagram showing a configuration of a measurement unit of a blood cell analyzer according to the embodiment.

The three measurement units 51, 51, 51 have the same configuration. FIG. 7 is a block diagram showing a configuration of the measurement unit 51. As shown in FIG. 7, the measurement unit 51 includes a specimen aspirating portion 511 for aspirating the blood being the specimen from the specimen container (blood collecting tube) T, a sample preparing portion 512 for preparing a measurement sample used in the measurement from the blood aspirated by the specimen aspirating portion 511, and a detecting portion 513 for detecting the blood cell from the measurement sample prepared by the sample preparing portion 512. The measurement unit 51 further includes a take-in port (not shown) for taking in the specimen container T accommodated in the sample rack L conveyed by the rack conveyance portion 35 of the specimen conveyance device 3 into the measurement unit 51, and a specimen container conveyance portion 515 for taking in the specimen container T from the sample rack L into the measurement unit 51 and conveying the specimen container T to the aspirating position by the specimen aspirating portion 511.

An aspirating tube (not shown) is arranged at the distal end of the specimen aspirating portion 511. The specimen aspirating portion 511 is movable in the vertical direction, and is moved to the lower side so that the aspirating tube passes through the lid CP of the specimen container T conveyed to the aspirating position to aspirate the blood inside.

The sample preparing portion 512 is connected to a reagent container 512a storing a staining reagent, a reagent container 512b storing a hemolyzing agent, and a reagent container 512c storing a diluted solution by way of a tube. The sample preparing portion 512 includes a pneumatic source 5120, so that the reagent can be aspirated (acquired) from the reagent containers 512a, 512b, 512c by the pressure generated by the pneumatic source. A barcode label (identifier) is attached to the reagent containers 512a, 512b, 512b, wherein information on the type of reagent (reagent name), lot number, manufactured date, and expiration date are recorded on the barcode label in a form of barcode. An IC chip may be used instead of the barcode label for the identifier. In this case, an IC chip reader is used for the reagent barcode reading portion 517.

The measurement unit 51 includes the reagent barcode reading portion 517. The reagent barcode reading portion 517 is a handy barcode reader, and the operator reads out the barcodes of the reagent containers 512a, 512b, 512c by holding the barcode reading portion 517 when reading the reagent barcode. The read information on the reagent type, lot number, manufactured date, and expiration date are transmitted to the information processing unit 52.

The detecting portion 513 is configured to perform the RBC (Red Blood Cell) detection and the PLT (Platelet) detection through the sheath flow DC detection method. In the RBC and the PLT detection by the sheath flow DC detection method, the measurement sample in which the specimen and the diluted solution stored in the reagent container 512c are mixed is measured, and the obtained measurement data is analyzed and processed by the information processing unit 52 to measure the RBC and the PLT. The detecting portion 513 can perform the HGB (Hemoglobin) detection through the SLS-hemoglobin method, and is configured to detect the WBC (White Blood Cell), NEUT (Neutrophil cell), LYMPH (Lymph cell), EO (Eosinophil leukocyte), BASO (Basophil leukocyte), and MONO (Monocyte) through the flow cytometry method using semiconductor laser. In the detecting portion 513, the detection method is different for the detection of the WBC not involving five categories of the white blood cells, that is, the detection of the WBC not involving the detection of the NEUT, LYMPH, EO, BASO, and MONO and the detection of the WBC involving five categories of the white blood cells. In the detection of the WBC not involving five categories of the white blood cells, the measurement sample in which the specimen, the hemolyzing agent stored in the reagent container 512b, and the diluted solution stored in the reagent container 512c are mixed is measured, and the obtained measurement data is analyzed and processed by the information processing unit 52 to measure the WBC. In the detection of the WBC involving five categories of the white blood cells, the measurement sample in which the staining reagent stored in the reagent container 512a, the hemolyzing agent stored in the reagent container 512b, and the diluted solution stored in the reagent container 512c are mixed is measured, and the obtained measurement data is analyzed and processed by the information processing unit 52 to measure the NEUT, LYMPH, EO, BASO, MONO, and WBC.

US Patent Application 2006-250604 is hereby incorporated by reference in its entirely as though fully and completely set forth herewith.

The specimen container conveyance portion 515 includes a hand portion 515a capable of gripping the specimen container T. The hand portion 515a includes a pair of gripping members arranged facing each other, and can approach or separate the gripping members to and from each other. The specimen container T can be gripped by approaching the relevant gripping members with the specimen container T in between. The specimen container conveyance portion 515 can move the hand portion 515a in the up and down direction and in the front and back direction (Y direction), and can oscillate the hand portion 515a. Thus, the specimen in the specimen container T can be stirred by gripping the specimen container T accommodated in the sample rack L and positioned at the supply position 35c with the hand portion 515a, taking out the specimen container T from the sample rack L by moving the hand portion 515a upward in the relevant state, and oscillating the hand portion 515a.

The specimen container conveyance portion 515 includes a specimen container setting portion 515b with a hole for receiving the specimen container T. The specimen container T gripped by the hand portion 515a described above is moved after stirring is completed, and the gripped specimen container T is inserted to the hole of the specimen container setting portion 515b. Thereafter, the specimen container T is released from the hand portion 515b by separating the gripping members, and the specimen container T is set in the specimen container setting portion 515b. The relevant specimen container setting portion 515b is horizontally movable in the Y direction by the power of the stepping motor (not shown). A barcode reading portion 516 is arranged inside the measurement unit 51. The specimen container setting portion 515b is movable to the barcode reading position 516a near the barcode reading portion 516 and the aspirating position 511a by the specimen aspirating portion 511. When the specimen container setting portion 515b is moved to the barcode reading position 516a, the set specimen container T is horizontally rotated by a rotation mechanism (not shown), and the specimen barcode is read by the barcode reading portion 516. Thus, even if the barcode label BL1 of the specimen container T is positioned on the opposite side with respect to the barcode reading portion 516, the barcode label BL1 can be directed towards the barcode reading portion 516 by rotating the specimen container T so that the specimen barcode can be read by the barcode reading portion 516. When the specimen container setting portion 515b is moved to the aspirating position, the specimen is aspirated from the set specimen container T by the specimen aspirating portion 511.

Figure 8:
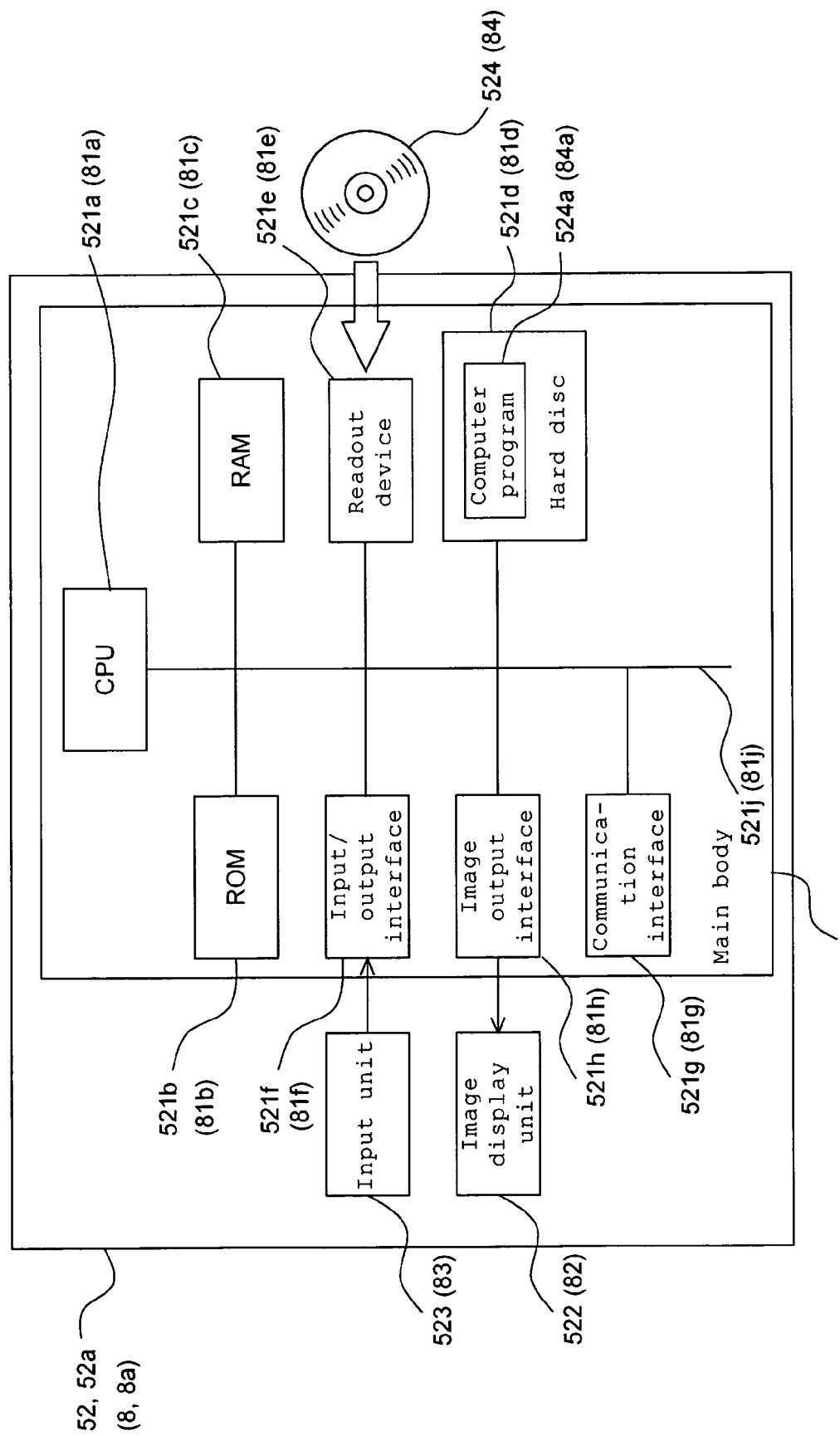
FIG. 8 is a block diagram showing a configuration of an information processing unit of the blood cell analyzer according to the embodiment.

The configuration of the information processing unit 52 will now be described. The information processing unit 52 is configured by a computer. FIG. 8 is a block diagram showing a configuration of the information processing unit 52. The information processing unit 52 is realized by a computer 52a. As shown in FIG. 8, the computer 52a includes a main body 521, an image display unit 522, and an input unit 523. The main body 521 includes a CPU 521a, a ROM 521b, a RAM 521c, a hard disc 521d, a readout device 521e, an input/output interface 521f, a communication interface 521g, and an image output interface 521h, wherein the CPU 521a, the ROM 521b, the RAM 521c, the hard disc 521d, the readout device 521e, the input/output interface 521f, the communication interface 521g, and the image output interface 521h are connected by a bus 521j.

The CPU 521a can execute the computer program loaded in the RAM 521c. The computer 52a functions as the information processing unit 52 by causing the CPU 521a to execute the computer program 524a for the specimen analysis and for the control of the measurement unit 51.

The ROM 521b is configured by mask ROM, PRM, EPROM, EEPROM, and the like, and is recorded with the computer program executed by the CPU 521a, the data used when executing the computer program, and the like.

The RAM 521c is configured by SRAM, DRAM, or the like. The RAM 521c is used to read out the computer program 524a recorded in the hard disc 521d. The RAM 521c is used as a work region of the CPU 521a when executing such computer programs.

The hard disc 521d is installed with various computer programs to be executed by the CPU 521a, and the data used for the execution of the computer program such as an operating system and an application program. The computer program 524a to be hereinafter described is also installed in the hard disc 521d.

The readout device 521e is configured by flexible disc drive, CD-ROM drive, DVD-ROM, or the like. The readout device 521e can read out computer program or data recorded in a portable recording medium 524. The portable recording medium 524 stores the computer program 524a for causing the computer to function as the information processing unit 52, wherein the computer 52a reads out the computer program 524a from the portable recording medium 524, and installs the computer program 524a in the hard disc 521d.

The computer program 524a is not limited to being provided by the portable recording medium 524, and may be provided through an electrical communication line from an external device communicably connected to the computer 52a by the electrical communication line (wired or wireless). For instance, the computer program 524a may be stored in a hard disc of a server computer on the Internet, and the computer 52a may access the server computer and download the computer program to install in the hard disc 521d.

The hard disc 521d is installed with a multi-task operating system such as Windows (registered trademark) manufactured and sold by US Microsoft Co. In the following description, the computer program 524a according to the present embodiment operates on the operating system.

Figure 9:
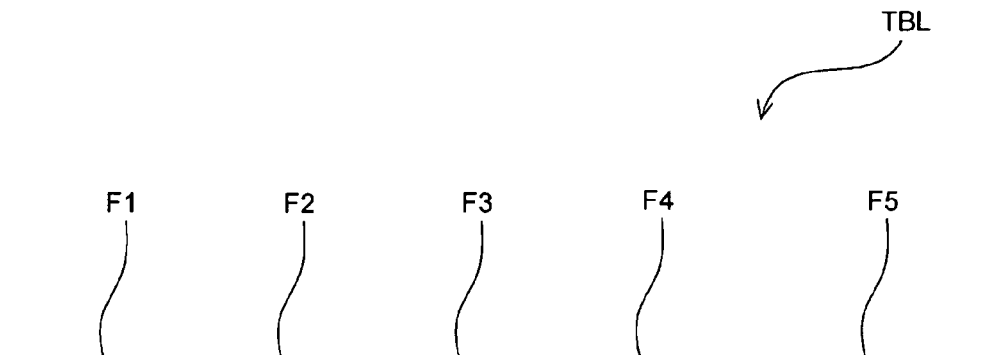
FIG. 9 is a schematic view showing a structure of a reagent management table.

The hard disc 521d includes a reagent management table TBL. FIG. 9 is a schematic view showing a structure of the reagent management table TBL. The reagent management table TBL is data for managing the measurement unit ID for specifying the measurement unit, the reagent type, the lot number, the manufactured date, and the expiration date of the reagent containers 512a, 512b, 512c. The measurement unit ID is information used to distinguish the three measurement units 51, 51, 51. Each measurement unit 51 is assigned a unique measurement unit ID. The measurement unit ID of "M1", "M2", and "M3" are assigned to the measurement units 51, 51, 51 according to the present embodiment in order from the upstream side to the downstream side of conveyance.

The reagent management table TBL includes a field F1 of measurement unit ID, a field F2 of reagent type, a field F3 of lot number, a field F4 of manufactured date, and a field F5 of expiration date. Each row in the figure corresponds to the reagent at one to one. That is, the measurement unit ID, the reagent type, the lot number, the manufactured date, and the expiration date in one row correspond to one reagent. In such reagent management table TBL, the reagent type, the lot number, the manufactured date, and the expiration date read by the reagent barcode reading portion 517 are stored in the fields F2 to F5 in the reagent management table TBL. The information input from the input unit 523 by the operator is stored for the measurement unit ID in the field F1.

The input/output interface 521f is configured by serial interface such as USB, IEEE1394, RS-232C; parallel interface such as SCSI, IDE, IEEE1284; analog interface including D/A converter, A/D converter and the like. The input/output interface 521f is connected with the input unit 523 such as a keyboard and a mouse, and the user can input data to the computer 52a by using the input unit 523. The input/output interface 521f is connected to three measurement units 51, 51, 51. The data can be transmitted and received with each of the three measurement units 51, 51, 51.

The communication interface 521g is an Ethernet interface. The communication interface 521g is connected to the system control device 8 through the LAN. The computer 52a can transmit and receive data with the system control device 8 connected to the LAN using a predetermined communication protocol by the communication interface 521g. The communication interface 521g is communicably connected to the host computer 9 and each specimen conveyance device 3, 3, 3 through the LAN.

The image output interface 521h is connected to the image display unit 522 configured by LCD, CRT, or the like, and outputs a video signal corresponding to the image data provided from the CPU 521a to the image display unit 522. The image display unit 522 displays an image (screen) according to the input video signal.

<Configuration of Smear Producing Device 6>

The smear producing device 6 aspirates the blood specimen, drops the blood specimen on a slide glass, thinly spreads the blood specimen on the slide glass, dries the blood specimen, and then supplies staining fluid to the slide glass to stain the blood on the slide glass to thereby produce the smear.

Figure 10:
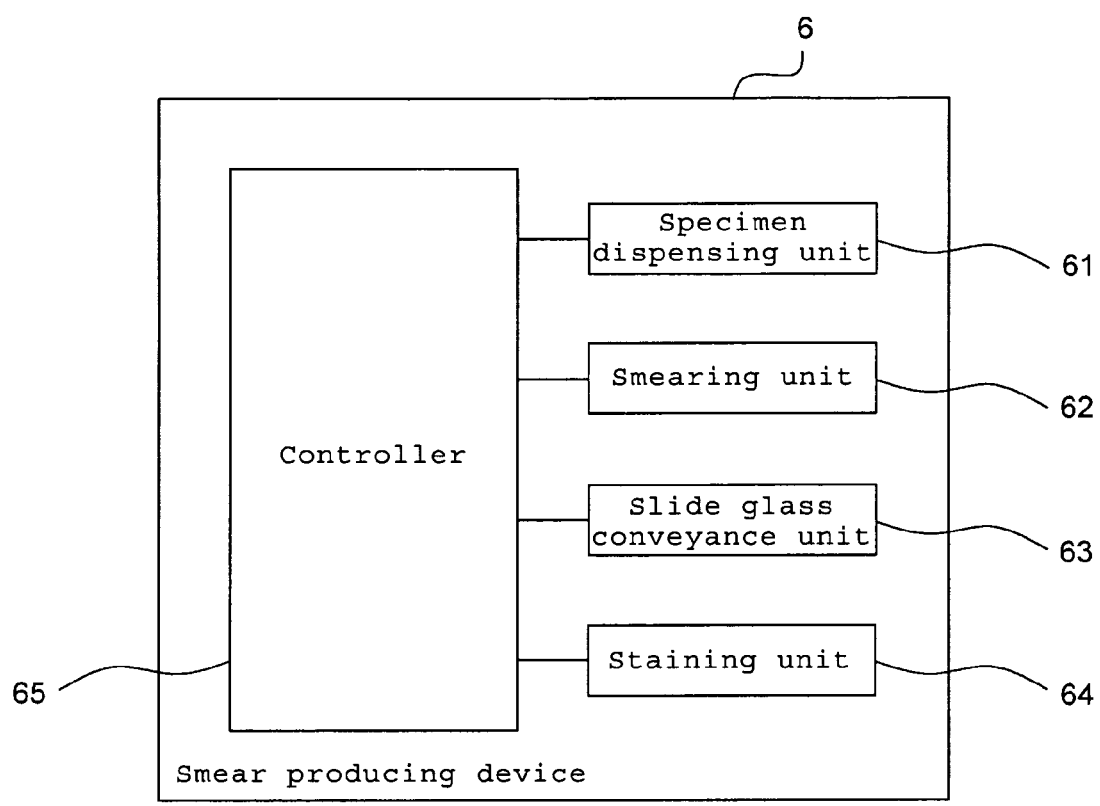
FIG. 10 is a block diagram showing a schematic configuration of a smear producing device according to the embodiment.

FIG. 10 is a block diagram showing a schematic configuration of the smear producing device 6. As shown in FIG. 10, the smear producing device 6 includes a specimen dispensing unit 61, a smearing unit 62, a slide glass conveyance unit 63, a staining unit 64, and a controller 65.

The specimen dispensing unit 61 includes an aspiration tube (not shown), which aspiration tube is pierced to the lid C of the specimen container T of the sample rack L conveyed on the measurement line 31a of the specimen conveyance device 3 to aspirate the blood specimen from the specimen container T. The specimen dispensing unit 61 is configured to drop the aspirated blood specimen on the slide glass. The smearing unit 62 is configured to smear and dry the blood specimen dropped onto the slide glass, and to print on the slide glass.

The slide glass conveyance unit 63 is provided to accommodate the slide glass smeared with the blood specimen by the smearing unit 62 in the cassette (not shown) and further convey such cassette. The staining unit 64 supplies the staining fluid to the slide glass in the cassette conveyed to the staining position by the slide glass conveyance unit 63. The controller 65 controls the specimen dispensing unit 61, the smearing unit 62, the slide glass conveyance unit 63, and the staining unit 64 according to a sample producing instruction provided from the specimen conveyance device 3, and executes the smear producing operation. The smear produced in such manner is sent to the blood cell image display device 7.

<Configuration of System Control Device 8>

The system control device 8 is configured by a computer, and controls the entire specimen processing system 1. The system control device 8 accepts the number of the sample rack L from the specimen inserting device 2, and determines the conveyance destination of the sample rack L.

The system control device 8 is configured by a computer 8a. As shown in FIG. 8, the computer 8a includes a main body 81, an image display unit 82, and an input unit 83. The main body 81 includes a CPU 81a, a ROM 81b, a RAM 81c, a hard disc 81d, a readout device 81e, an input/output interface 81f, a communication interface 81g, and an image output interface 81h, wherein the CPU 81a, the ROM 81b, the RAM 81c, the hard disc 81d, the readout device 81e, the input/output interface 81f, the communication interface 81g, and the image output interface 81h are connected by a bus 81j.

The hard disc 81d is installed with various computer programs to be executed by the CPU 81a, and the data used for the execution of the computer program, such as an operating system and an application program. The system control program 84a to be hereinafter described is also installed in the hard disc 81d. The hard disc 81d is also installed with a computer program to function as a clock, so that the CPU 81a can grasp the current time. The readout device 81e is configured by flexible disc drive, CD-ROM drive, DVD-ROM, or the like, and can read out computer program or data recorded in a portable recording medium 84. The portable recording medium 84 stores the system control program 84a for causing the computer to function as the system control device 8, wherein the computer 8a reads out the system control program 84a from the portable recording medium 84, and installs the system control program 84a in the hard disc 81d.

The input/output interface 81f is configured by serial interface such as USB, IEEE1394, RS-232C; parallel interface such as SCSI, IDE, IEEE1284; analog interface including D/A converter, A/D converter and the like. The input/output interface 81f is connected with the input unit 83 such as a keyboard and a mouse, and the user can input data to the computer 52a by using the input unit 83.

The communication interface 81g is an Ethernet (registered trademark) interface. The communication interface 81g is connected to the specimen inserting device 2, the specimen conveyance device 3, the specimen accommodating device 4, the information processing unit 52, and the host computer 9 through the LAN. The computer 8a can transmit and receive data with each device connected to the LAN using a predetermined communication protocol by the communication interface 81g.

Other configurations of the system control device 8 are similar to the configuration of the information processing unit 52, and thus the description thereof will be omitted.

<Configuration of Host Computer 9>

The host computer 9 is configured by a computer, and includes a CPU, a ROM, a RAM, a hard disc, a communication interface, and the like. The communication interface is connected to the LAN, and can communication with the system control device 8, the information processing unit 52 of the blood cell analyzer 5, the specimen inserting device 2, the specimen conveyance device 3, and the specimen accommodating device 4. The hard disc is stored with measurement orders. The measurement order contains information on the specimen ID and the measurement item to be conducted. When receiving request data of the measurement order including the specimen ID from another device, the host computer 9 reads out the measurement data corresponding to such specimen ID from the hard disc, and transmits to the device of the requesting source. Other configurations of the host computer 9 are similar to the configuration of other computers described above, and thus the description thereof will be omitted.

The operation of the specimen processing system 1 according to the present embodiment will be described below.

[Reagent Information Acquiring Operation]

Figure 11A:
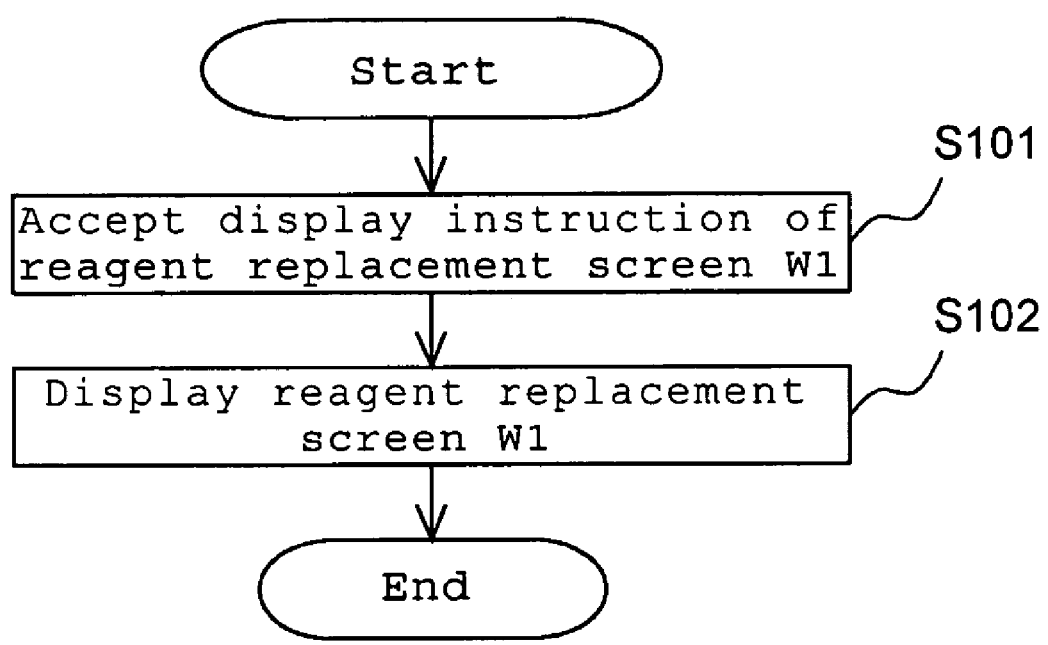
FIG. 11A shows a flowchart showing a flow of a reagent replacement screen displaying process of the information processing unit in the reagent information acquiring process.

First, the reagent information acquiring operation in which the system control device 8 acquires the reagent information when the reagent of the measurement unit 51 is replaced will be described. The reagent replacement is carried out using a reagent replacement screen W1 displayed on the information processing unit 52. FIG. 11A shows a flowchart showing a flow of the reagent replacement screen displaying process of the information processing unit 52 in the reagent information acquiring process. If the reagent needs to be replaced as there are no more reagent in the measurement unit 51 or the expiration has elapsed, the reagent is replaced. In this case, the operator operates the input unit 523 of the information processing unit 52 to input the display instruction of the reagent replacement screen to provide the display instruction of the reagent replacement screen to the CPU 521a (step S101). The computer program 524a executed by the CPU 521a of the information processing unit 52 is an event-driven program, wherein the process of step S102 is called out when an event of accepting the display instruction of the reagent replacement screen occurs in the CPU 521a.

Figure 12:
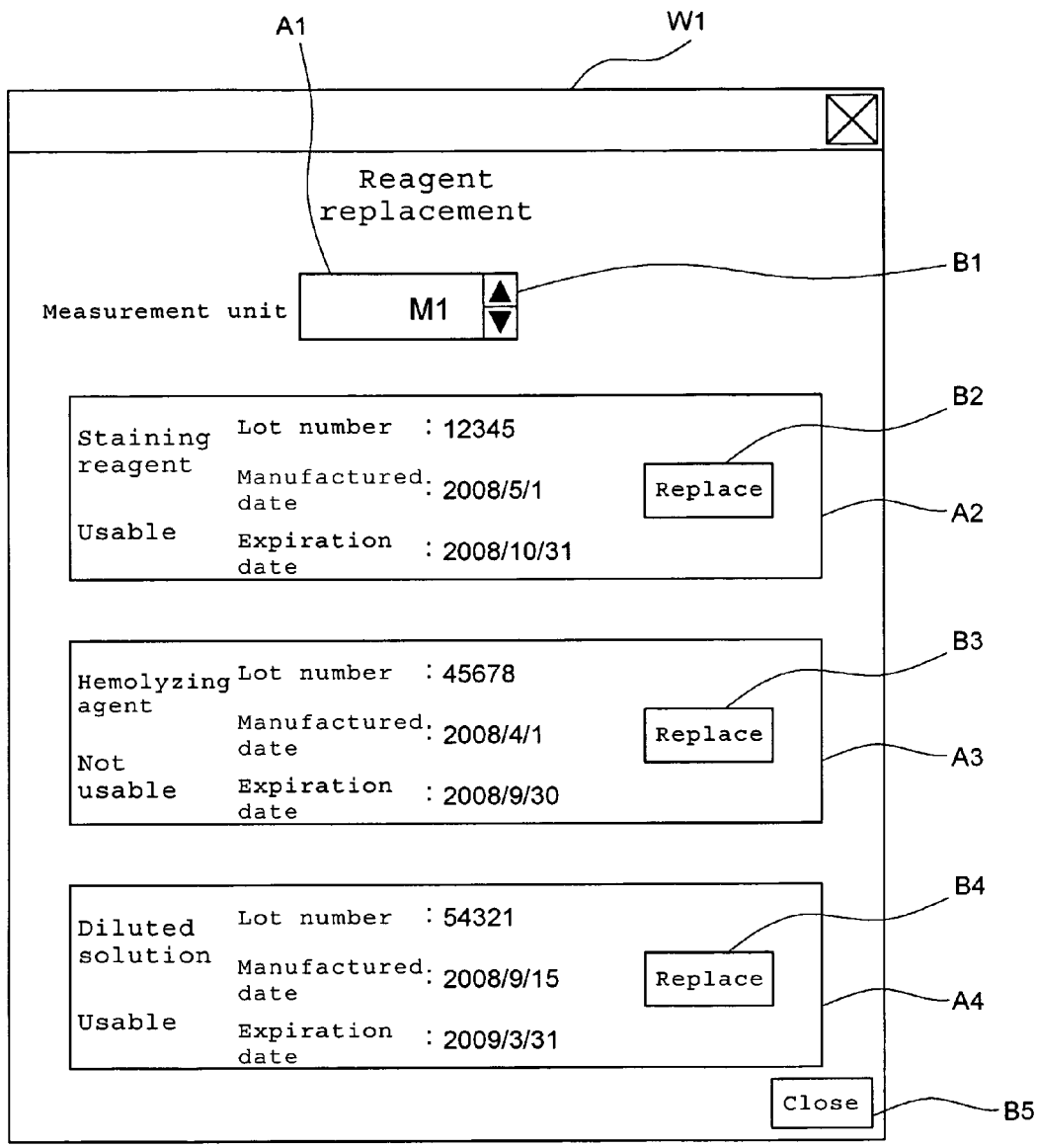
FIG. 12 is a view showing the reagent replacement screen of the information processing unit.

In step S102, the CPU 521a displays the reagent replacement screen on the image display unit 522 (step S102), and terminates the process. FIG. 12 is a view showing the reagent replacement screen. As shown in the figure, the reagent replacement screen W1 includes an area A1 for displaying the measurement unit ID, an area A2 for displaying the state of the staining reagent, an area A3 for displaying the state of the hemolyzing agent, and an area A4 for displaying the state of the diluted solution. A select button B1 for selecting the measurement unit ID is displayed in the area A1 for displaying the measurement unit ID. The measurement unit ID can be selected by the operator by operating the select button B1 with the input unit 523. The area A1 also displays the measurement unit ID being selected at the time. When the operator selects the measurement unit ID, the state of the reagent of the measurement unit 51 corresponding to the selected measurement unit ID is displayed in the areas A2 to A4. That is, the screen display of the reagent replacement screen W1 switches by the selection of the measurement unit ID.

In a state the reagent replacement screen W1 is displayed, "usable" is displayed in the area A2 of the reagent replacement screen W1 if the expiration date of the staining reagent of the measurement unit 51 selected in the reagent replacement screen W1 has not elapsed. If the expiration date of the staining reagent has elapsed, "not usable" is displayed in the area A2. Similarly, "usable" is displayed in the area A3 if the expiration date of the hemolyzing reagent of the selected measurement unit 51 has not elapsed, and "not usable" is displayed in the area A3 if the expiration date of the hemolyzing reagent has elapsed. Similarly, "usable" is displayed in the area A4 if the expiration date of the diluted solution of the selected measurement unit 51 has not elapsed, and "not usable" is displayed in the area A4 if the expiration date of the diluted solution has elapsed. Selectable reagent replace instruction buttons B2 to B4 are respectively arranged in the reagent state display areas A2 to A4 of the reagent replacement screen W1.

Figure 11B:
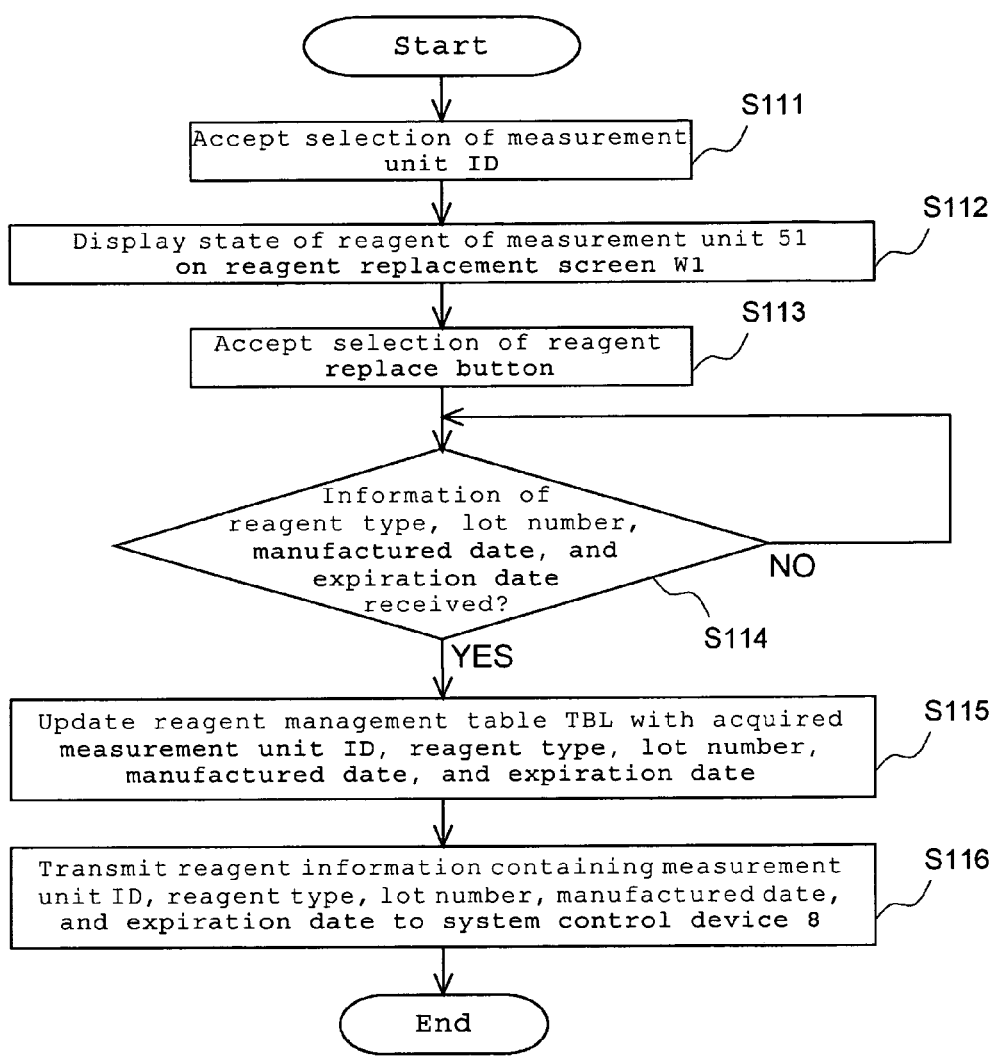
FIG. 11B shows a flowchart showing a flow of the reagent replacement process of the information processing unit in the reagent information acquiring process.

FIG. 11B shows a flowchart showing a flow of the reagent replacement process of the information processing unit 52 in the reagent information acquiring process. When the reagent replacement screen W1 is displayed, the operator selects the select button B1 to select the measurement unit ID of the measurement unit in which the state of the reagent is desirably checked. When an event of accepting the selection of the measurement unit ID occurs (step S111), the CPU 521a displays the state of the reagent of the relevant measurement unit 51 in the areas A2 to A4 in the reagent replacement screen W1 based on the information of the reagent management table TBL (step S112).

If "not usable" is displayed in one of the reagent state display areas A2 to A4, or if there is no more reagent, the operator performs the replacement task of the reagent. In the reagent replacement task, the operator selects the reagent replace button of the reagent to be replaced by operating the input unit 523. The CPU 521a thereby accepts the selection of the reagent replace button (step S113). When an event of accepting the selection of the reagent replace button occurs, the CPU 521a waits for the reception of the information of the reagent type, the lot number, the manufactured date, and the expiration date of the reagent (NO in step S114). After selecting the reagent replace button, the operator detaches the reagent container from the measurement unit 51, to which the reagent container to be replaced is connected, and replaces with a new reagent container. The reagent barcode printed on the barcode label of the new reagent container is then read by the barcode reading portion 517. The information on the reagent type, the lot number, the manufactured date, and the expiration date acquired by the barcode reading portion 517 are then provided to the CPU 521a.

When accepting the information on the reagent type, the lot number, the manufactured date, and the expiration date (YES in step S114), the CPU 521a registers the measurement unit ID selected in the reagent replacement screen W1, as well as, the acquired information on the reagent type, the lot number, the manufactured date, and the expiration date in the reagent management table TBL (step S115). Thereafter, the CPU 521a transmits the reagent information including the measurement unit ID, the reagent type, the lot number, the manufactured date, and the expiration date registered in the reagent management table TBL to the system control device 8 (step S116), and terminates the process. The hard disc 81d of the system control device 8 stores the reagent information on the three measurement units 51, 51, 51. The system control device 8 receives the reagent information transmitted from the information processing unit 52, and stores the measurement unit ID, the reagent type, the lot number, the manufactured date, and the expiration date contained in the reagent information in the hard disc 81d in correspondence to each other to update the reagent information of the three measurement units 51, 51, 51 stored in the hard disc 81d to the most recent state.

Figure 11C:
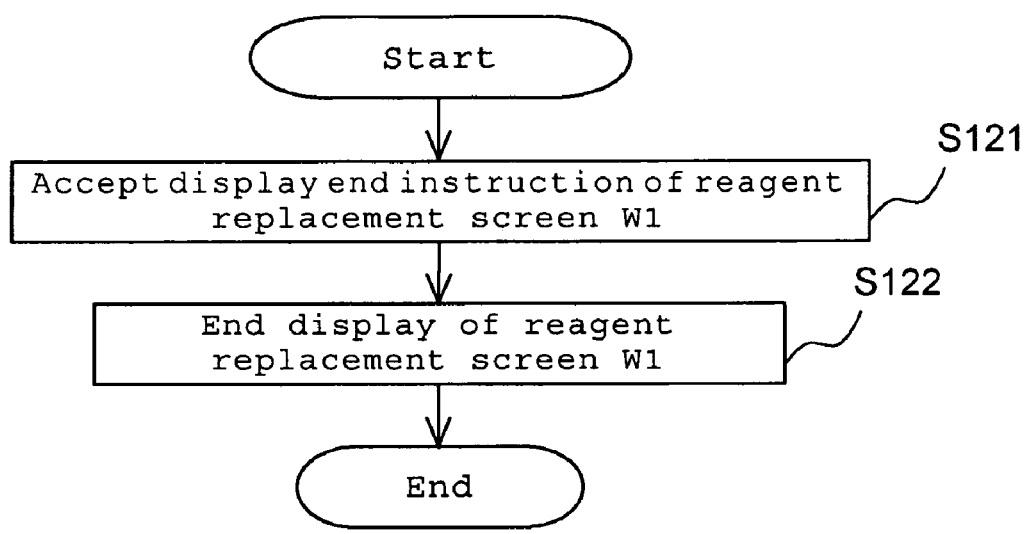
FIG. 11C shows a flowchart showing a flow of the reagent replacement screen display end process of the information processing unit in the reagent information acquiring process.

As shown in FIG. 12, a close button B5 selectable for accepting a display end instruction of the reagent replacement screen W1 is arranged in the reagent replacement screen W1, wherein the operator selects the close button B5 when the reagent replacement task is ended. FIG. 11C shows a flowchart showing a flow of the reagent replacement screen display end process of the information processing unit 52 in the reagent information acquiring process. When an event of accepting the selection of the close button B5 occurs (step S121), the CPU 521a ends the display of the reagent replacement screen W1 (step S122), and terminates the process.

[Conveyance Mode Setting Operation]

The conveyance mode setting operation of the specimen processing system 1 will now be described. The specimen processing system 1 can set the conveyance mode of either a first conveyance mode of determining the conveying destination of the specimen based on the reagent information, or a second conveyance mode of determining the conveying destination of the specimen without based on the reagent information, and perform the conveyance of the specimen by such conveyance mode. The setting of the conveyance mode is performed in the system control device 8.

Figure 13A:
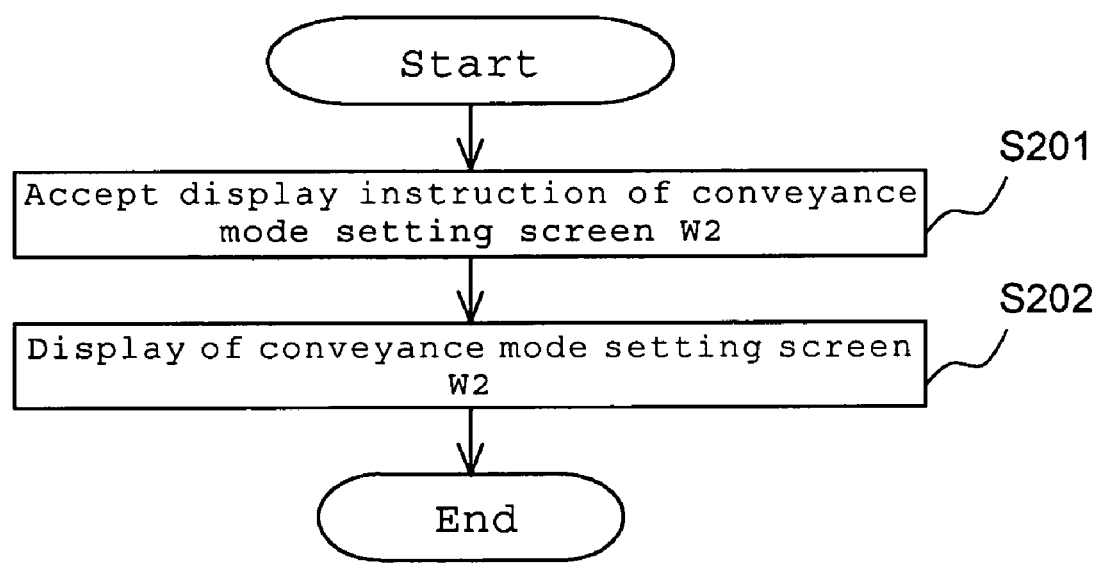
FIG. 13A shows a flowchart showing the procedures of the conveyance mode setting screen displaying process of the system control device.

FIG. 13A shows a flowchart showing the procedures of the conveyance mode setting screen displaying process of the system control device 8. When performing the setting of the conveyance mode, the operator operates the input unit 83 of the system control device 8 to input the display instruction of the conveyance mode setting screen. The display instruction of the conveyance mode setting screen is then provided to the CPU 81a (step S201). The computer program 84a executed by the CPU 81a of the system control device 8 is an event-driven program, wherein the process of step S202 is called out when an event of accepting the display instruction of the conveyance mode setting screen occurs in the CPU 81a.

Figure 14:
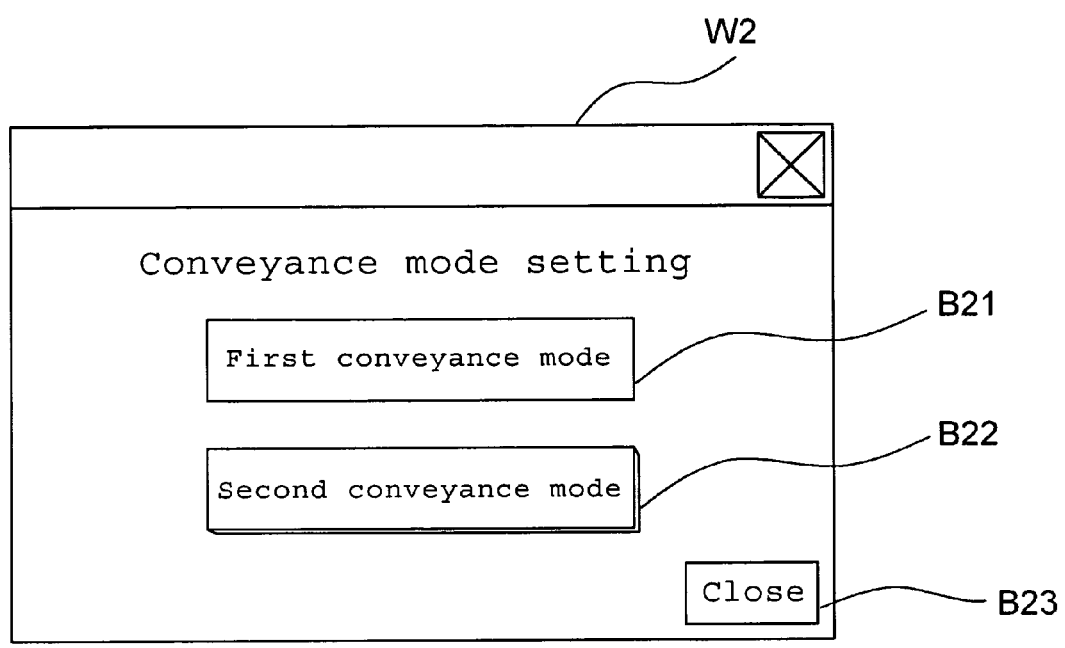
FIG. 14 is a view showing the conveyance mode setting screen of the system control device.

In step S202, the CPU 81a displays the conveyance mode setting screen on the image display unit 82 (step S202), and terminates the process. FIG. 14 is a view showing the conveyance mode setting screen. As shown in the figure, the conveyance mode setting screen W2 includes a first conveyance mode select button B21 for selecting the first conveyance mode (mode of preferentially conveying the specimen to the measurement unit 51 in which the expiration date of the reagent is approaching), and a second conveyance mode select button B22 for selecting the second conveyance mode (mode of evenly conveying the specimen to the three measurement units 51, 51, 51). Each of the first conveyance mode select button B21 and the second conveyance mode select button B22 can be selected by having the operator perform a predetermined operation (e.g., click left button of the mouse) on the input unit 83. As shown in the figure, a close button B23 selectable for accepting the display end instruction of the conveyance mode setting screen W2 is arranged in the conveyance mode setting screen W2.

Figure 13B:
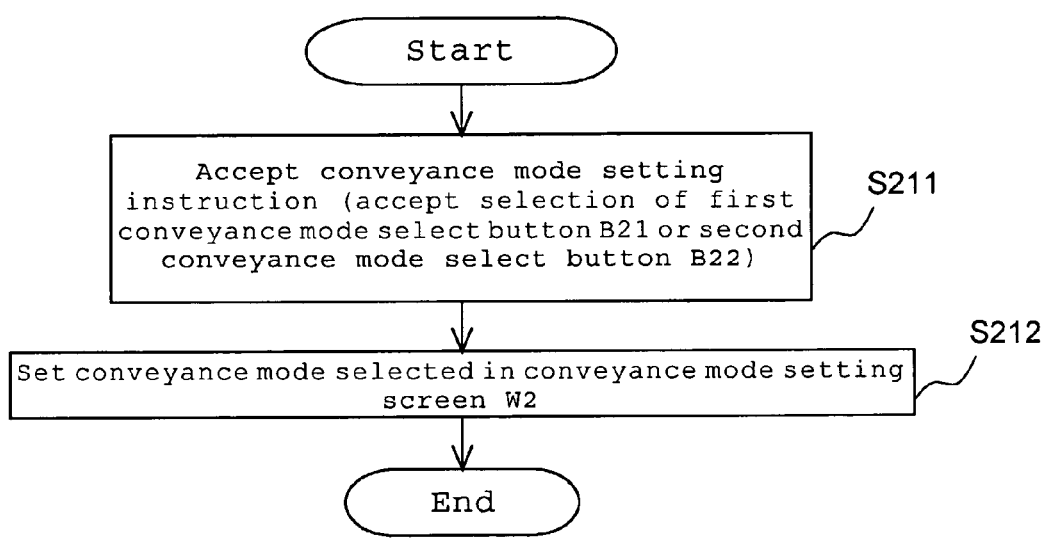
FIG. 13B shows a flowchart showing the procedures of the conveyance mode setting process of the system control device.

FIG. 13B shows a flowchart showing the procedures of the conveyance mode setting process in the conveyance mode setting screen. In a state the conveyance mode setting screen W2 is displayed, the operator selects the desired conveyance mode button from the first conveyance mode select button B21 or the second conveyance mode select button B22, and provides the setting instruction of the conveyance mode by the selection of the button to the CPU 81a (step S211). The selected button switches to a display different from the display of a case of not selected (e.g., display is made with the image of a state in which the button is projected when not selected, and display is made with the image of a state in which the button is pushed when selected). When an event of accepting the selection of either the first conveyance mode select button B21 or the second conveyance mode select button B22 occurs, the CPU 81a sets the selected conveyance mode (step S212). This process is performed by setting the conveyance mode flag arranged in the hard disc 81d. That is, the conveyance mode flag is set to "0" when the first conveyance mode is selected, the conveyance mode flag is set to "1" when the second conveyance mode is selected. Thereafter, the CPU 81a terminates the process.

Figure 13C:
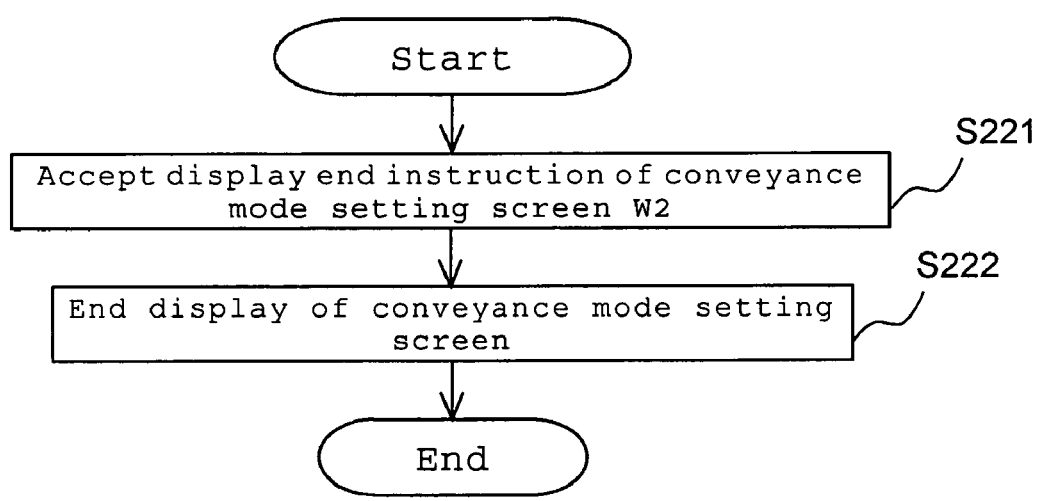
FIG. 13C shows a flowchart showing the procedures of the display end process of the conveyance mode setting screen of the system control device.

FIG. 13C shows a flowchart showing the procedures of the display end process of the conveyance mode setting screen. After the setting of the conveyance mode is ended, the operator selects the close button B23. When an event of accepting the selection of the close button B23 occurs (step S221), the CPU 81a ends the display of the conveyance mode setting screen W2 (step S222), and terminates the process.

[Specimen Conveying Operation]

<Operation of Specimen Inserting Device 2>

The operator places the sample rack L accommodating the specimen container T in the specimen sending unit 21a, operates the operation panel (not shown) of the specimen sending unit 21a, and gives an instruction to start the analysis to the specimen analyzing system 1. The controller of the specimen sending unit 21a accepts the instruction to start the analysis, and starts to move the sample rack L. The sample rack L placed on the specimen sending unit 21a is moved to the back side on the specimen sending unit 21a, and thereafter, the sample rack L is moved towards the left, and provided to the barcode reading unit 22.

The sample rack L introduced to the barcode reading unit 22 is moved by every one pitch towards the left on the conveyance path by the controller of the barcode reading unit 22. The rack barcode of the sample rack L and the specimen barcode of the specimen container T are read by the barcode reader. The sample rack is then further moved towards the left, and the sample rack L is moved to the specimen sending unit 21b. The controller of the specimen sending unit 21b moves the received sample rack L. The specimen inserting device 2 then transmits the convey-out request data including the read rack ID and the specimen ID to the system control device 8, and waits for the convey-out instruction data transmitted from the system control device 8. When receiving the convey-out instruction data from the system control device 8, the specimen inserting device 2 conveys the specimen rack L out to the adjacent specimen conveyance device 3, and transmits the convey-out complete data to the system control device 8.

<Operation of System Control Device 8>

The operation of the system control device 8 will now be described. The system control device 8 receives the convey-out request data from the specimen inserting device 2, and determines the conveying destination of the sample rack L by using the specimen ID contained in the convey-out request data. The operation will be specifically described below.

Figure 15A:
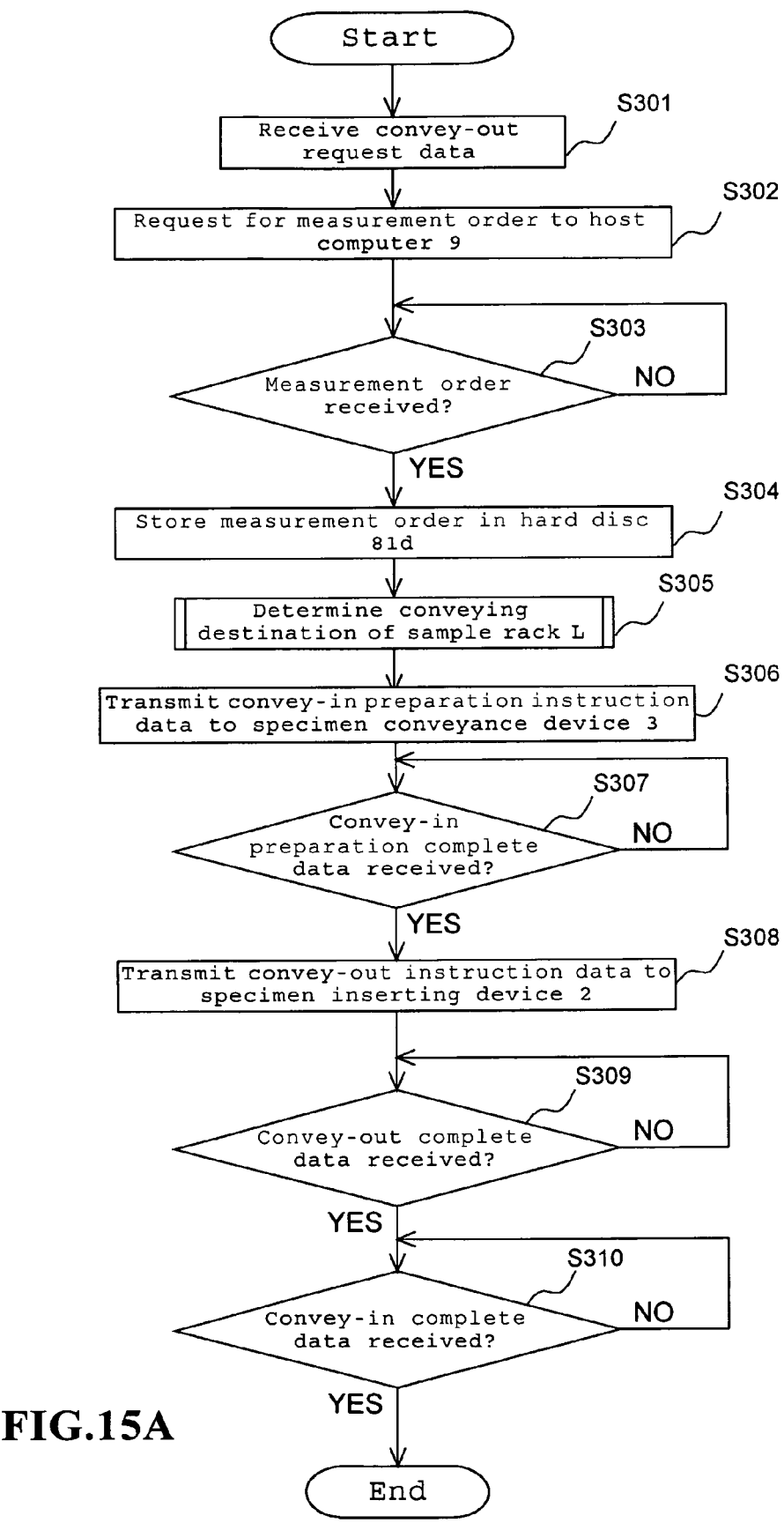
FIG. 15A shows a flowchart showing the procedures of the first conveyance instructing process of the system control device.

FIG. 15A shows a flowchart showing the procedures of the first conveyance instructing process of the system control device 8. In the first conveyance instructing process, the conveying destination of the sample rack L is determined, and the conveyance instruction is given to the specimen conveyance device 3 arranged in front of the M1 measurement unit 51. The convey-out request data transmitted from the specimen inserting device 2 is received by the communication interface 81g of the system control device 8 (step S301). When an event of receiving the convey-out request data occurs in the CPU 81a, the process of step S302 is called out.

In step S302, the CPU 81a transmits all specimen IDs contained in the received convey-out request data, and requests for a measurement order corresponding to the specimen ID to the host computer 9 (step S302). The CPU 81a waits for the reception of the measurement order (NO in step S303), and when receiving the measurement order transmitted from the host computer 9 at the system control device 8 (YES in step S303), stores the received measurement order in the hard disc 81d in correspondence to the rack ID (step S304). The CPU 81a then determines the conveying destination of the sample rack L based on the measurement item and/or the expiration date of the reagent contained in each received measurement order (step S305).

Figure 15B:
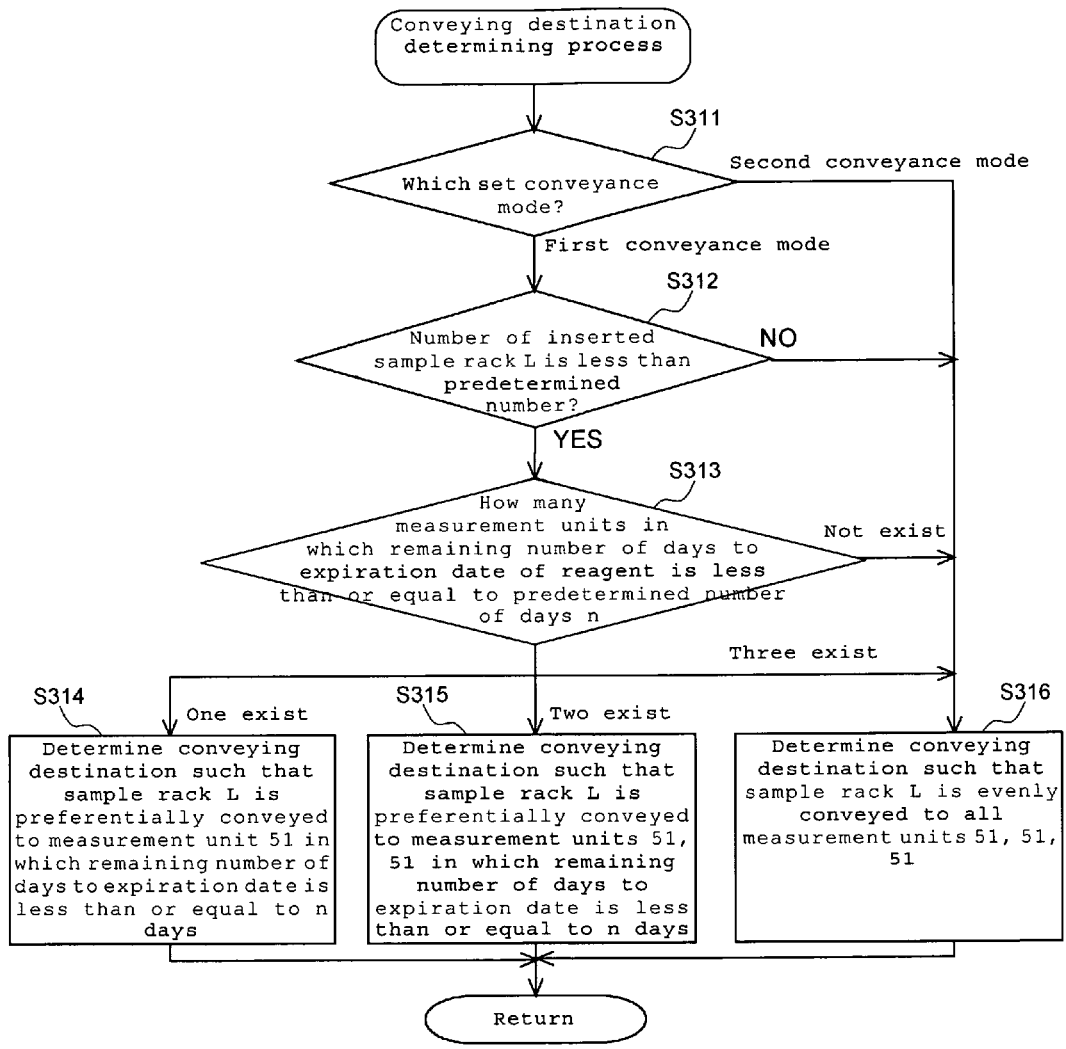
FIG. 15B shows a flowchart showing the procedures of the conveying destination determining process.

The conveying destination determining process of step S305 will be described. FIG. 15B shows a flowchart showing the procedures of the conveying destination determining process. The CPU 81a first references the conveyance mode flag, and determines whether the set conveyance mode is the first conveyance mode or the second conveyance mode (step S311). If the first conveyance mode is set ("first conveyance mode" in step S311), the CPU 81a determines whether the number of sample racks L received from the specimen inserting device 2 is smaller than a predetermined number (step S312). If the number of sample racks L placed in the specimen inserting device 2 is smaller than the predetermined number in step S312 (YES in step S312), the CPU 81a references the reagent information stored in the hard disc 81d, and determines how many of the three measurement units 51, 51, 51 exists in which the remaining number of days until the expiration date of the reagent used in the measurement item of the searched measurement order is less than or equal to a predetermined number n of days (step S313). For instance, if the remaining number of days until the expiration date of the staining reagent of M1 is less than or equal to n days, and other reagents in which the remaining number of days until the expiration date is less than or equal to n days do not exist, and if the measurement order includes items (NEUT, LYMPH, EO, BASO, MONO) of five categories of the white blood cells, the sample rack L is preferentially conveyed to the M1.

In step S313, the CPU 81a compares the current time (date in the present embodiment) with the expiration date of the respective reagent, and acquires the remaining number of days until the expiration date for each reagent. If the remaining number of days until the expiration date of the reagent of one measurement unit 51 is less than or equal to n days ("one exists" in step S313), the CPU 81a determines the conveying destination of the sample rack L such that the sample rack L is preferentially conveyed to the measurement unit 51 attached with the reagent which remaining number of days until the expiration date is less than or equal to n days (step S314). In this process, the conveying destination of the sample rack L is determined such that the sample rack L is conveyed in the order of M1, M1, M2, M3, M1, M1, M2, M3, . . . if the remaining number of days until the expiration date of the reagent of M1 is less than or equal to n days (i.e., in a repeated cycle in which the sample rack L is conveyed to M1 to M3 one at a time, the number of times to convey the sample rack L to M1 in one cycle is increased by one time). That is, if the sample rack L is conveyed to M1 two times consecutively immediately before, M2 is determined as the conveying destination of the sample rack L for this time. If the sample rack L is conveyed to M3 and M1 immediately before, M1 is determined as the conveying destination of the sample rack L for this time, and if the sample rack L is conveyed to M2 and M3 immediately before, M1 is again determined as the conveying destination of the sample rack L for this time. If the sample rack L is conveyed to M1 and M2 immediately before, M3 is determined as the conveying destination of the sample rack L for this time. After the process of step S314, the CPU 81a returns the process to the call-out address of the conveying destination determining process S303.

If the remaining number of days until the expiration date of the reagents of two measurement units 51, 51 is less than or equal to n days ("two exist" in step S313) in step S313, the CPU 81a determines the conveying destination of the sample rack L such that the sample rack L is preferentially conveyed to the measurement units 51, 51 attached with the reagents which remaining number of days until the expiration date is less than or equal to n days (step S315). In this process, the conveying destination of the sample rack L is determined such that the sample rack L is conveyed in the order of M1, M1, M2, M2, M3, M1, M1, M2, M2, M3, ... if the remaining number of days until the expiration date of the reagent of M1 and M2 is less than or equal to n days (i.e., in a repeated cycle in which the sample rack L is conveyed to M1 to M3 one at a time, the number of times to convey the sample rack L to M1 and M2 in one cycle is increased by one time). That is, if the sample rack L is conveyed to M1 two times consecutively immediately before, M2 is determined as the conveying destination of the sample rack L for this time, and if the sample rack L is conveyed to M1 and M2 immediately before, M2 is again determined as the conveying destination of the sample rack L for this time. If the sample rack L is conveyed to M3 and M1 immediately before, M1 is determined as the conveying destination of the sample rack L for this time, and if the sample rack L is conveyed to M2 and M3 immediately before, M1 is again determined as the conveying destination of the sample rack L for this time. If the sample rack L is conveyed to M2 two times consecutively immediately before, M3 is determined as the conveying destination of the sample rack L for this time. After the process of step S315, the CPU 81a returns the process to the call-out address of the conveying destination determining process S303.

If the second conveyance mode is set in step S311 ("second conveyance mode" in step S311), the CPU 81a determines the conveying destination of the sample rack L such that the sample rack L is evenly conveyed to all the measurement units 51, 51, 51 (step S316) if the number of sample racks L placed on the specimen inserting device 2 is greater than or equal to the predetermined number in step S312 (NO in step S312), the remaining number of days until the expiration date of the reagents of the three measurement units 51, 51, 51 is less than or equal to n days in step S313 ("three exist" in step S313), or the measurement unit in which the remaining number of days until the expiration date of the reagent is less than or equal to n days does not exist in step S313 ("not exist" in step S313). In this process, the conveying destination is determined such that the sample rack L is conveyed in the order of M1, M2, M3, M1, M2, M3, ... (i.e., cycle of conveying the sample rack L to M1 to M3 one at a time is repeatedly executed). That is, if the sample rack L is conveyed to M1 immediately before, M2 is determined as the conveying destination of the sample rack L for this time, and if the sample rack L is conveyed to M2 immediately before, M3 is determined as the conveying destination of the sample rack L for this time. If the sample rack L is conveyed to M3 immediately before, M1 is determined as the conveying destination of the sample rack L for this time. After the process of step S316, the CPU 81a returns the process to the call-out address of the conveying destination determining process 5303.

The CPU 81a transmits the convey-in preparation instruction data of the sample rack L based on the determined conveying destination (step S306) to the specimen conveyance device 3 adjacent to the specimen inserting device 2 (i.e., specimen conveyance device 3 on the rightmost side in FIG. 1). The convey-in preparation instruction data contains data (hereinafter referred to as "use conveyance line instruction data") indicating the conveyance line (measurement line L1 or skip line L2) for conveying the sample rack L in the specimen conveyance device 3, and measurement order of each specimen of the sample rack L. That is, if the conveying destination of the sample rack L is the measurement unit 51 of M1, the data indicating the measurement line L1 is set as the use conveyance line instruction data in the convey-in preparation instruction data. If the measurement unit 51 of M2 or M3 is determined as the conveying destination, the data indicating the skip line L2 is set as the use conveyance line instruction data in the convey-in preparation instruction data. The specimen conveyance device 3 that has received the convey-in preparation instruction data executes the preparation operation (operation capable of receiving the sample rack L) of the conveyance mechanism shown by the use conveyance line instruction data contained in the convey-in preparation instruction data, and thereafter, transmits the convey-in preparation complete data.

The CPU 81a waits for the convey-in preparation complete data from the specimen conveyance device 3 (NO in step S307). When the convey-in preparation complete data is transmitted from the specimen conveyance device 3, and the convey-in preparation complete data is received by the system control device 8 (YES in step S307), the CPU 81a transmits the convey-out instruction data of the sample rack L to the specimen inserting device 2 (step S308). When receiving the convey-out instruction data, the specimen inserting device 2 conveys out the sample rack L to the specimen conveyance device 3, and transmits the convey-out complete data. The CPU 81a waits for the convey-out complete data from the specimen inserting device 2 (NO in step S309). When the convey-out complete data is transmitted from the specimen inserting device 2 and the convey-out complete data is received by the system control device 8 (YES in step S309), the CPU 81a waits for the convey-in complete data from the specimen conveyance device 3 (NO in step S310). When the convey-in complete data is transmitted from the specimen conveyance device 3 and the convey-in complete data is received by the system control device 8 (YES in step S310), the CPU 81a terminates the process.

Figure 16:
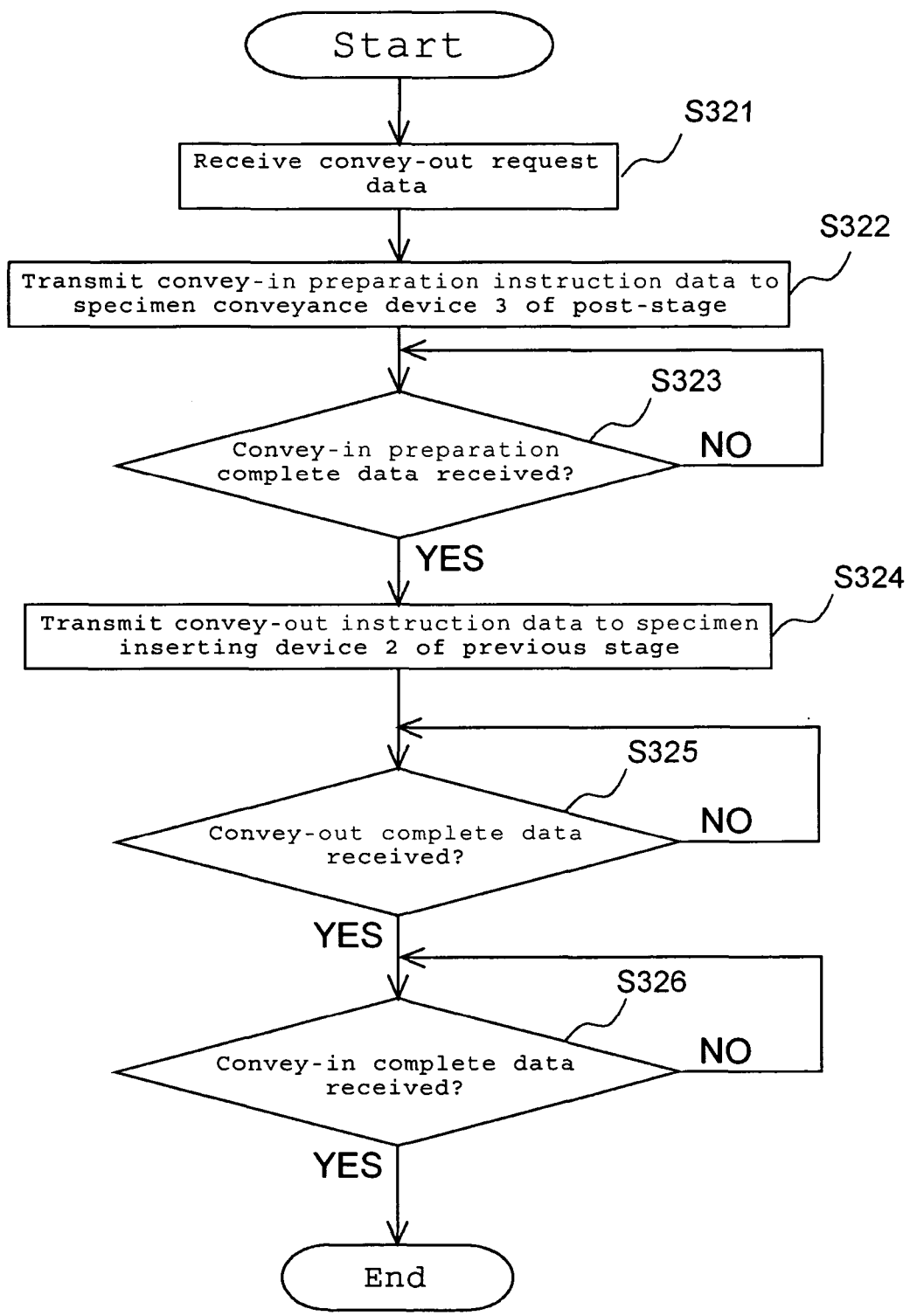
FIG. 16 shows a flowchart showing the procedures of the second conveyance instructing process of the system control device.

The second conveyance instructing process of the system control device 8 will now be described. In the second conveyance instructing process, the conveyance instruction is provided to the specimen conveyance device 3 arranged in front of the measurement unit 51 of M2 or M3. FIG. 16 shows a flowchart showing the procedures of the second conveyance instructing process. When the sample rack L is conveyed by the specimen conveyance device 3, and the sample rack L reaches the convey-out position for conveying out the sample rack L to the specimen conveyance device 3 of the post-stage (or the specimen conveyance device 301), the convey-out request data containing the rack ID of the sample rack L is transmitted from the specimen conveyance device 3. The convey-out request data transmitted from the specimen conveyance device 3 is received by the communication interface 81g of the system control device 8 (step S321). When an event of receiving the convey-out request data from the specimen conveyance device 3 occurs in the CPU 81a, the process of step S322 is called out.

In step S322, the CPU 81a transmits the convey-in preparation instruction data of the sample rack L based on the conveying destination determined in the conveying destination determining process to the specimen conveyance device 3 of the post-stage of the specimen conveyance device 3 (step S322). The convey-in preparation instruction data is similar to the convey-in preparation instruction data, described above, and thus the description thereof will be omitted.

The CPU 81a waits for the convey-in preparation complete data from the specimen conveyance device 3 (NO in step S323). When the convey-in preparation complete data is transmitted from the specimen conveyance device 3, and the convey-in preparation complete data is received by the system control device 8 (YES in step S323), the CPU 81a transmits the convey-out instruction data of the sample rack L to the specimen conveyance device 3 of the previous stage (convey-out side) (step S324). When receiving the convey-out instruction data, the specimen conveyance device 3 of the previous stage conveys the sample rack L out to the specimen conveyance device 3 of the post-stage, and transmits the convey-out complete data. The CPU 81a waits for the convey-out complete data from the specimen conveyance device 3 of the previous stage (NO in step S325), and when the convey-out complete data is transmitted from the specimen conveyance device 3 of the previous stage, and the convey-out complete data is received by the system control device 8 (YES in step S325), the CPU 81a waits for the convey-in complete data from the specimen conveyance device 3 of the post-stage (NO in step S326). When the convey-in complete data is transmitted from the specimen conveyance device 3 of the post-stage, and the convey-in complete data is received by the system control device 8 (YES in step S326), the CPU 81a terminates the process.

<Operation of Controller 32 of Specimen Conveyance Device 3>

Figure 17A:
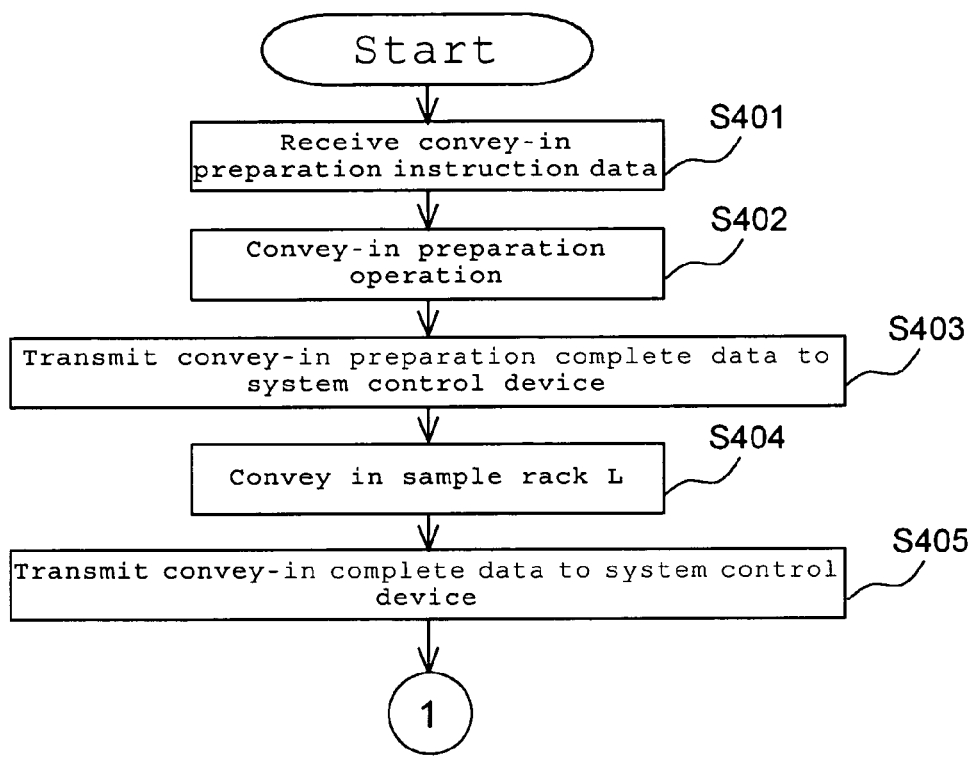
FIG. 17A shows a flowchart (first half) showing the flow of the control process of the conveyance mechanism by the controller of the specimen conveyance device.
Figure 17B:
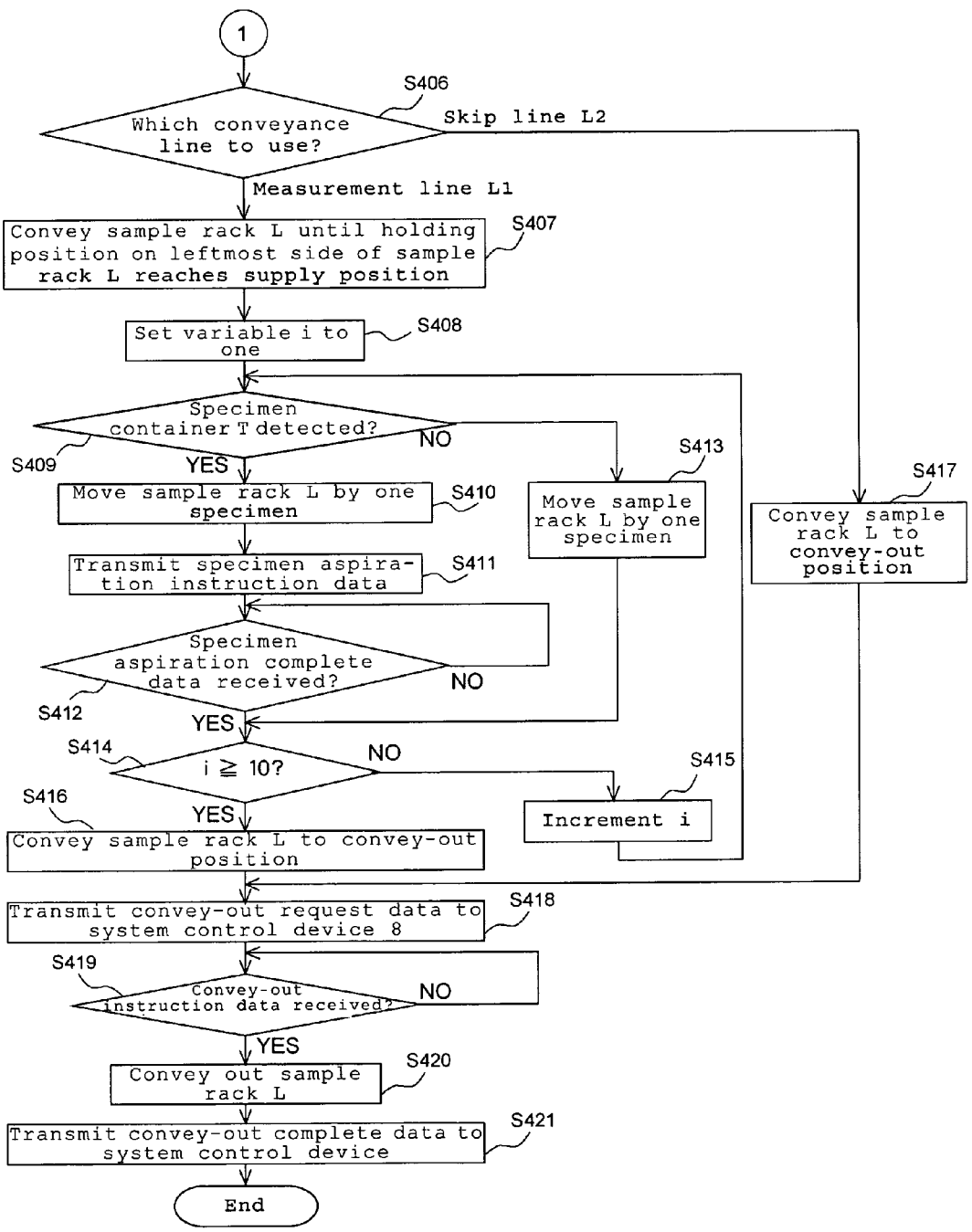
FIG. 17B shows a flowchart (second half) showing the flow of the control process of the conveyance mechanism by the controller of the specimen conveyance device.

The operation of the controller 32 of the specimen conveyance device 3 arranged in front of the measurement unit 51 will be described below. FIG. 17A and FIG. 17B show flowcharts showing the flow of the control process of the conveyance mechanism 31 by the controller 32. The convey-in preparation instruction data transmitted from the system control device 8 is received by the controller 32 (step S401). The conveyance control program executed by the CPU of the controller 32 is an event-driven program, and the process of step S402 is called out when an event of receiving the convey-in preparation instruction data occurs in the controller 32.

In step S402, the controller 32 drives the belt 321a of the conveyance mechanism 31 and executes the convey-in preparation operation (step S402). When the convey-in preparation is completed, the controller 32 transmits the convey-in preparation complete data for notifying that the convey-in preparation has completed to the system control device 8 (step S403).

In response to the transmission of the convey-in preparation complete data, the sample rack L is conveyed out from the device of the previous stage, and the sample rack L is conveyed into the conveyance mechanism 31 (step S404). When the conveying in of the sample rack L is completed, the controller 32 transmits the convey-in complete data for notifying the completion of conveying in the sample rack L to the system control device 8 (step S405).

The controller 32 determines whether or not the use conveyance line instruction data contained in the convey-in preparation instruction data indicates the measurement line L1 or the skip line L2, that is, which of the measurement line L1 or the skip line L2 is the conveyance line to be used (step S406). If the use conveyance line instruction data contained in the convey-in preparation instruction data indicates the measurement line L in step S406, that is, if the measurement line L1 is the conveyance line to be used ("measurement line L1" in step S406), the controller 32 controls the conveyance mechanism 31, and moves the holder positioned at the leftmost side in FIG. 3 until reaching the specimen container detection position (step S407). The controller 32 then sets the variable i indicating the holding position of the specimen container T in the sample rack L to 1 (step S408), determines whether the specimen container T is detected at the specimen container detection position by the specimen container sensor 38 (step S409), moves the sample rack L towards the left by one specimen (step S410) if the specimen container T is detected (YES in step S409), and transmits the specimen aspirate instruction data indicating the aspirating instruction of the specimen to the information processing unit 51 (step S411). The specimen container T detected by the specimen container sensor 38 is thereby positioned at the specimen supply position 35c, and the specimen is aspirated, as hereinafter described. The controller 32 waits until receiving the specimen aspiration complete data (NO in step S412), and advances the process to step S414 when receiving the specimen aspiration complete data (YES in step S412).

If the specimen container T is not detected in step S409 (NO in step S409), the controller 32 moves the sample rack L towards the left by one specimen (step S413), and advances the process to step S414. In step S414, the controller 32 determines whether or not i is greater than or equal to ten (step S414), and increments i by one (step S415) if i is smaller than ten (NO in step S414), and returns the process to step S409.

If i is greater than or equal to ten in step S414 (YES in step S414), the controller 32 controls the conveyance mechanism 31 so that the sample rack L reaches the convey-out position for conveying out the sample rack L (step S416). Thereafter, the controller 32 advances the process to step S418.

If the use conveyance line instruction data contained in the convey-in preparation instruction data indicates the skip line L2 in step S406, that is, if the skip line L2 is the conveyance line to be used ("skip line L2" in step S406), the controller 32 controls the conveyance mechanism 31, moves the sample rack L onto the skip line L2, and reaches the sample rack L to the convey-out position for conveying out the sample rack L (step S417). Thereafter, the controller 32 advances the process to step S418.

In step S418, the controller 32 transmits the convey-out request data containing the rack ID assigned to the sample rack L to the system control device 8 (step S418). Thereafter, the controller 32 waits for the convey-out instruction data from the system control device 8 (NO in step S419), and when receiving the convey-out instruction data (YES in step s419), drives the stepping motor 321b to convey out the sample rack L to the adjacent specimen conveyance device 3 (step S420), and transmits the convey-out complete data to the system control device 8 (step S421). The controller 32 then terminates the process.

<Operation of Blood Cell Analyzer 5>

The operation of the blood cell analyzer 5 will now be described. The information processing unit 52 controls the operation of the measurement units 51, 51, 51 and measures the specimen, and analyzes the measurement data obtained by the measurement.

Figure 18A:
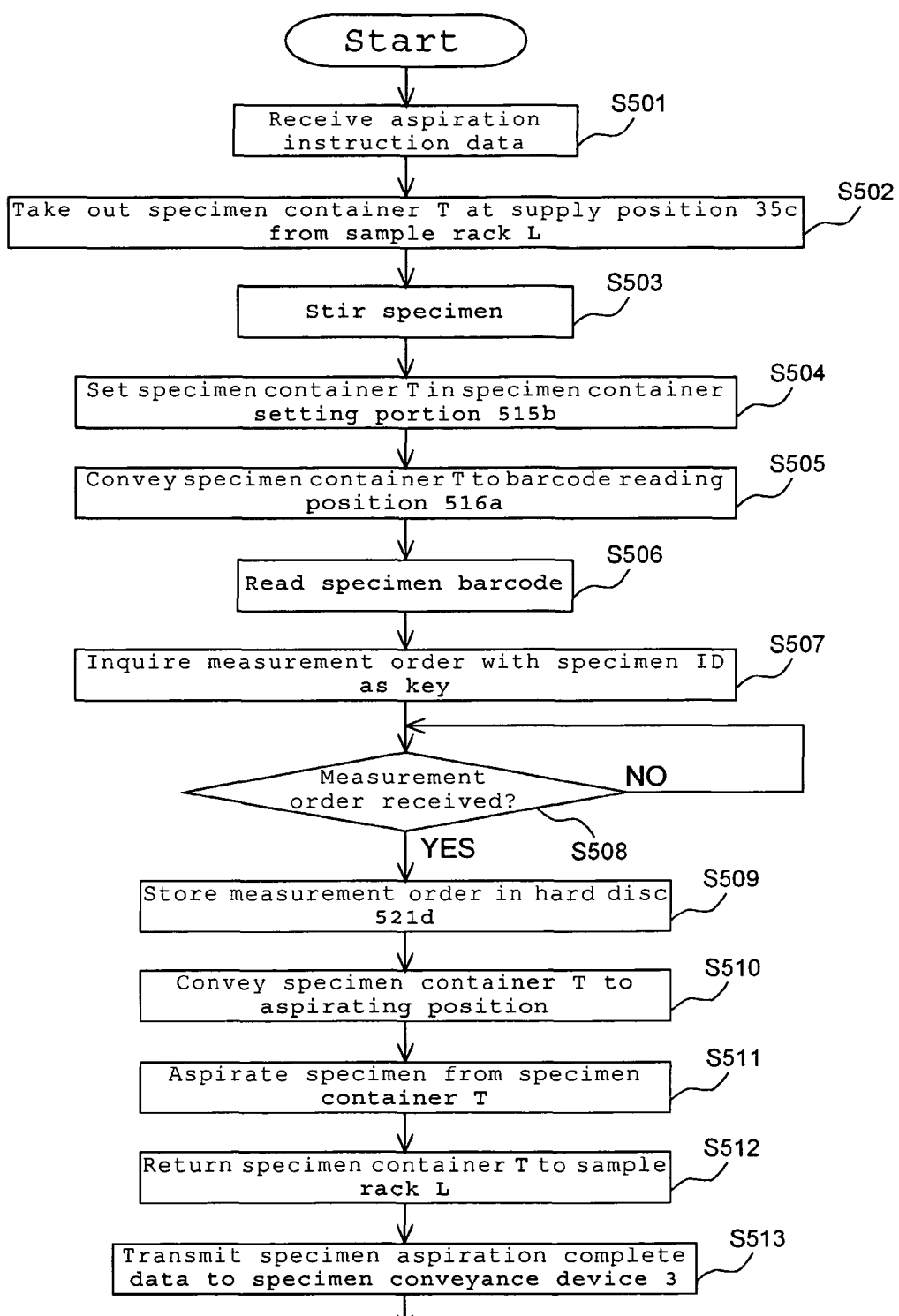
FIG. 18A shows a flowchart (first half) showing the procedures of the analyzing operation of the specimen by the blood cell analyzer according to the embodiment.
Figure 18B:
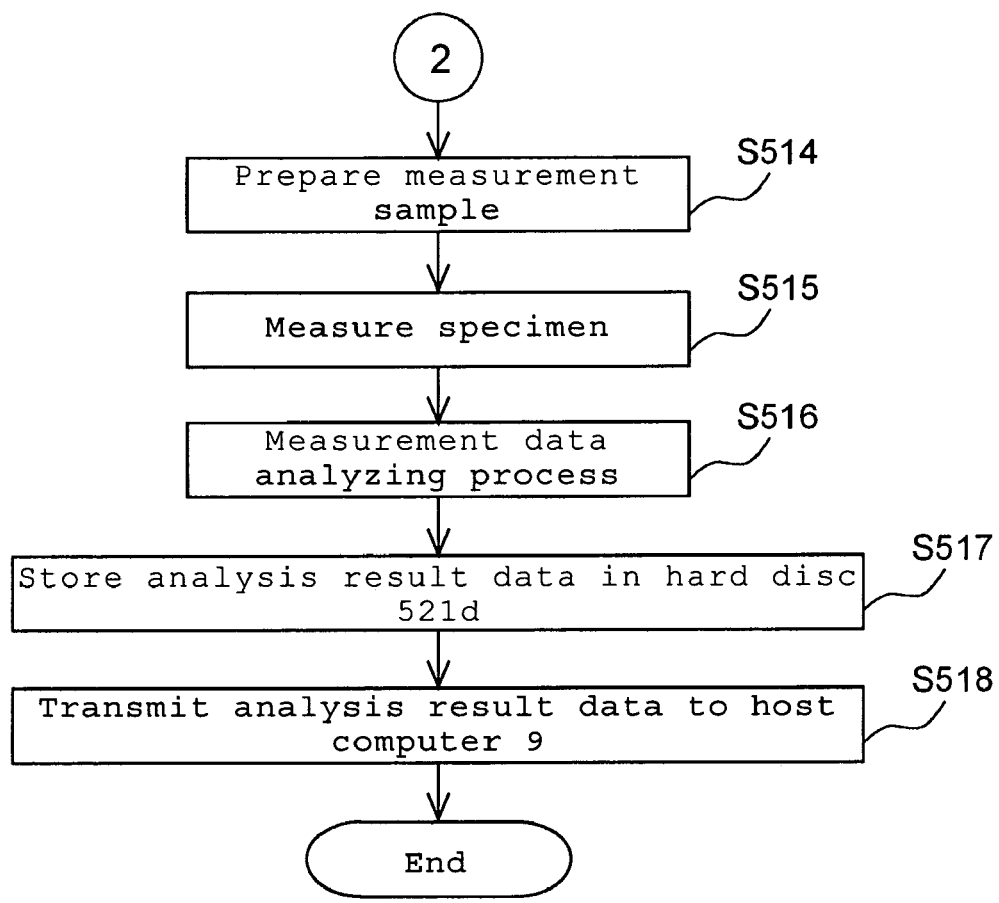
FIG. 18B shows a flowchart (second half) showing the procedures of the analyzing operation of the specimen by the blood cell analyzer according to the embodiment.

FIG. 18A and FIG. 18B are flowcharts showing the procedures of the analyzing operation of the specimen by the blood cell analyzer 5 according to the present embodiment. First, the information processing unit 52 receives the aspiration instruction data transmitted from the controller 32 of the specimen conveyance device 3 (step S501). The process of step S502 is called out when an event of receiving the aspiration instruction data occurs in the CPU 521a. The aspiration instruction data contains the measurement unit ID of the measurement unit 51 to be operated.

In step S502, the CPU 521a controls the specimen container conveyance portion 515, takes out the specimen container T at the supply position 35c from the sample rack L (step S502), controls the hand portion 515a to oscillate the specimen container T, and stirs the specimen inside (step S503). The CPU 521a controls the hand portion 515a and sets the specimen container T in the specimen container setting portion 515b (step S504), controls the specimen container conveyance portion 515, and conveys the specimen container T to the barcode reading position 516a (step S505). The CPU 521a then reads the specimen barcode of the specimen container T with the barcode reading portion 516, and acquires the specimen ID (step S506). The CPU 521a then causes the communication interface 521g to transmit the order request data containing the specimen ID to the host computer 9 (step S507), and inquires the measurement order. The CPU 521a then waits for the reception of the measurement order (NO in step S508), and when the measurement order transmitted from the host computer 9 is received by the communication interface 521g of the information processing unit 52 (YES in step S508), stores the received measurement order in the hard disc 521d (step S509).

The CPU 521a controls the specimen container conveyance portion 515 and conveys the specimen container T to the aspirating position (step S510), controls the specimen aspirating portion 511, and aspirates the specimen of the amount necessary for the measurement item contained in the stored measurement order from the specimen container T (step S511). After the aspiration of the specimen is completed, the CPU 521a controls the specimen container conveyance portion 515, returns the specimen container T to the sample rack L (step S512), and transmits the specimen aspiration complete data to the specimen conveyance device 3 conveying the sample rack L (step S513). The sample rack L is conveyed by the rack conveyance portion 35 in the above manner.

The CPU 521a controls the sample preparing portion 512, prepares the measurement sample according to the measurement item (step S514), supplies the measurement sample to the detecting portion 513, and measures the specimen with the detecting portion 513 (step S515). The CPU 521a then acquires the measurement data output from the detecting portion 513. The CPU 521a executes the analyzing process of the measurement data (step S516), categorizes the blood cells contained in the specimen and counts the number of blood cells for every type, and creates a scattergram in which the categorized blood cells are color coded by every type. The analysis result data generated by the analyzing process of the measurement data is stored in the hard disc 521a with the patient information and the like contained in the measurement order (step S517), and transmitted to the host computer 9 (step S518). The host computer 9 integrates the analysis result data to the measurement order and stores the same in the hard disc. After the process of step S518 is completed, the CPU 521a terminates the process.

<Operation of Specimen Conveyance Device 301>

The sample rack L sent from the specimen conveyance device 3 positioned on the most downstream side in the conveying direction is introduced to the rack slider 303. The details will be omitted, but the rack slider 303 accepts the instruction from the system control device 8, and sends the sample rack L to either the measurement line 302a or the skip line 302b of the conveyor 302. If the sample rack L is conveyed into the measurement line 302a, the controller of the conveyor 302 operates the measurement line 302a, and conveys the sample rack L such that the specimen container T of smear producing target is positioned at the supply position of supplying the specimen to the smear producing device 6. After the supply of the specimen to the smear producing device 6 is completed, the measurement line 302a is driven and the sample rack L is conveyed out to the specimen accommodating device 4. If the sample rack L is conveyed into the skip line 302b, the controller of the conveyor 302 operates the skip line 302b, conveys the sample rack L onto the skip line 302, and conveys the sample rack L to the specimen accommodating device 4.

<Operation of Specimen Accommodating Device 4>

The sample rack L sent out from the specimen conveyance device 301 is introduced to the specimen accommodating device 4. The specimen accommodating device 4 conveys and accommodates the relevant sample rack L on the rack mounting part.

According to the above configuration, the system control device 8 determines the conveying destination such that the reagent can be efficiently used according to the state of the reagent of respective measurement units 51, 51, 51. Therefore, the process of the specimen can be performed while efficiently using the reagent compared to the prior art.

In the specimen processing system 1 according to the present embodiment, the specimen can be preferentially supplied to the measurement unit, which expiration date of the reagent is approaching, of the three measurement units 51, 51, 51. The consumption amount of the reagent which expiration date is approaching thus becomes greater than the consumption amount of other reagents, and the waste of reagents can be resolved such as completely using up the reagent before the expiration date expires and the relevant reagent cannot be used or reducing the remaining amount of the reagent which expiration date has expired.

In the specimen processing system 1 according to the present embodiment, the first conveyance mode of preferentially conveying the specimen to the measurement unit 51 which expiration date of the reagent is approaching, and the second conveyance mode being a mode of conveying the specimen evenly to three measurement units 51, 51, 51 can be selectively set, and thus the reagent can be efficiently used if the first conveyance mode is set, and the number of processing per unit time (processing throughput) in the entire specimen processing system 1 can be increased as much as possible if the second conveyance mode is set.

In the specimen processing system 1 according to the present embodiment, the sample rack L is evenly conveyed to three measurement units 51, 51, 51 when the number of sample racks L mounted on the specimen inserting device 2 is greater than or equal to a predetermined number. If the sample rack L to be conveyed exists in great number, that is, if the specimen waiting to be processed exists in great number, the sample rack L is evenly conveyed to three measurement units 51, 51, 51, and the processing ability in the entire specimen processing system 1 can be enhanced, whereby great number of specimens can be processed in a short period of time and the specimen processing system 1 can be efficiently operated.

(Other Embodiments)

In the above-described embodiment, a configuration of preferentially conveying the sample rack L to the measurement unit 51 in which the remaining number of days until the expiration date of the reagent is less than a predetermined number of days has been described, but this is not the sole case. The sample rack L may be preferentially conveyed to the measurement unit 51 in which the remaining number of days until the expiration date of the reagent is the least in the plurality of measurement units 51, 51, 51.

In the above-described embodiment, a configuration of determining the conveying destination of the sample rack L based on the expiration date of the reagent has been described, but this is not the sole case. The conveying destination of the sample rack L may be determined based on the manufactured date of the reagent such as preferentially conveying the sample rack L to the measurement unit 51 in which a period of longer than or equal to a predetermined period has elapsed from the manufactured date of the reagent or preferentially conveying the sample rack L to the measurement unit 51 in which the longest period has elapsed from the manufactured date of the reagent of the plurality of measurement units 51, 51, 51. The predetermined period after opening the reagent is generally defined as the usable period of the reagent. The conveying destination of the sample rack L may be determined based on the usage period of the reagent such as preferentially conveying the sample rack L to the measurement unit 51 in which the remaining number of days to the usable period of the reagent (i.e., expiration date after opening) is less than a predetermined number of days, or preferentially conveying the sample rack L to the measurement unit in which the remaining number of days to the usable period (i.e., expiration date after opening) is the least of the plurality of measurement units 51, 51, 51.

In the above-described embodiment, the reagent containers 512a, 512b, 512c are connected to the sample preparing portion 512 with a tube, and the reagent is supplied from the reagent containers 512a, 512b, 512c to the sample preparing portion 512 through the tube, but this is not the sole case. A bottle-shaped reagent container may be mounted on the measurement unit, so that the reagent in the reagent container may be aspirated with a pipette and the reagent may be dispensed to another container such as a cuvette or a chamber.

In the above-described embodiment, the first conveyance mode of preferentially conveying the specimen to the measurement unit 51 in which the expiration date of the reagent is approaching, and the second conveyance mode being a mode of conveying the specimen evenly to three measurement units 51, 51, 51 are selectively settable, but this is not the sole case. The specimen may always be preferentially conveyed to the measurement unit 51 in which the expiration date of the reagent is approaching without providing the conveyance mode of evenly conveying the specimen to the three measurement units 51, 51, 51. The second conveyance mode may be a mode of preferentially conveying the specimen to the measurement unit 51 that has not processed the specimen. The processing ability of the specimen thus can be enhanced.

In the above-described embodiment, a configuration of conveying two sample racks L successively to the measurement unit 51 to which the sample rack L is to be preferentially conveyed in the repeatedly executed cycle of sequentially conveying the sample rack L to three measurement units 51, 51, 51 in the a state in which the first conveyance mode is set has been described, but is not limited thereto. The priority may be set in plural stages according to the remaining number of days until the expiration date, and the number of sample racks L to successively convey per one cycle to the measurement unit 51 to which the sample rack L is to be preferentially conveyed may be changed according to the priority. For instance, the priority may be divided into three levels of high, middle, and low, wherein two sample racks L are successively conveyed per one cycle to the target measurement unit 51 when the priority is low level, three sample racks L are successively conveyed per one cycle to the target measurement unit 51 when the priority is middle level, and four sample racks L are successively conveyed per one cycle to the target measurement unit 51 when the priority is high level. The user may input the priority to the system control device 8, and the system control device 8 may set the priority. For instance, two sample racks L are successively conveyed to the measurement unit 51 to which the sample rack L is to be preferentially conveyed if the priority set by the user is "2", and three sample racks L are successively conveyed per one cycle to the target measurement unit 51 if the priority set by the user is "3". The priority may be set by a real number such as "1.5". In this case, with two cycles as a unit, one sample rack L is conveyed in the first cycle to the measurement unit 51 to be prioritized, and two sample racks L are successively conveyed in the second cycle. A fine priority setting is thus enabled.

The operator may change the setting of the number of sample racks L to successively convey per one cycle to the measurement unit 51 to which the sample rack L is to be preferentially conveyed.

In the above-described embodiment, the configurations of the three measurement units 51, 51, 51 are the same, but are not limited thereto. The specimen processing system may include a plurality of measurement units having a common measurement item having a different configuration. For instance, the multiple item blood cell analyzers XE-5000 and XT-2000i manufactured by Sysmex Co. include common measurement items such as WBC (White Blood Cell), NEUT (Neutrophil cell), LYMPH (Lymph cell), EO (Eosinophil leukocyte), BASO (Basophil leukocyte), and MONO (Monocyte). The specimen processing system may include the XE-5000 and the XT-2000i, and the measurement items common in both devices may preferentially convey the specimen to be measured to the measurement unit in which the expiration date of the reagent is approaching.

In the above-described embodiment, a configuration in which the specimen processing system 1 includes the blood cell analyzer 5 for categorizing the blood cells contained in the specimen and counting the blood cells for every blood cell type has been described, but this is not the sole case. The specimen processing system may include a plurality of measurement units of a specimen analyzer other than the blood cell analyzer such as an immune analyzer, a blood coagulation measurement device, a biochemical analyzer, and a urine analyzer, and convey the blood specimen or the urine specimen to the measurement unit of the specimen analyzer.

In the embodiment described above, a configuration of determining the conveying destination of the sample rack by having the CPU 81a execute the system control program of the system control device 8 has been described, but is not limited thereto. The process of determining the conveying destination of the sample rack L may be executed by a dedicated hardware such as FPGA or ASIC capable of executing a process similar to the conveying destination determining program of the sample rack L.

In the above-described embodiment, a configuration in which all the processes of the computer program 84a are executed by a single computer 8a has been described, but is not limited thereto, and a distributed system of executing the processes similar to the computer program 84a in a distributed manner by a plurality of devices (computers) may be adopted.

In the above-described embodiment, a configuration in which the CPU 81a of the system control device 8 determines the conveying destination of the specimen and the controller 32 of the conveyance device 3 controls the operation of the conveyance mechanism 31 has been described, but is not limited thereto, and the CPU 81a of the system control device 8 may execute both the determination of the conveying destination and the operation control of the conveyance mechanism 31.

In the above-described embodiment, a configuration of acquiring the expiration date of the reagent as the reagent information and determining the conveying destination has been described, but is not limited thereto, and a configuration of acquiring lot information (lot number) of the reagent as the reagent information and determining the conveying destination based on the lot information may be adopted. In this case, the CPU 81a of the system control device 8 may transmit the lot information to the server computer installed in a facility of the manufacturer of the reagent. The server computer merely needs to store the lot information of all manufactured reagents, so that whether or not the lot information transmitted by the CPU 81a is stored can be judged. The server computer transmits the information indicating that the relevant reagent is manufactured by a predetermined manufacturer to the CPU 81a if the transmitted lot information is stored, and transmits the information indicating that the relevant reagent is manufactured other than by the predetermined manufacturer to the CPU 81a if the transmitted lot information is not stored. When receiving the information indicating that the relevant reagent is manufactured other than by the predetermined manufacturer, the CPU 81a excludes the measurement unit 51 connected with the reagent having such lot information from the conveying destination and displays a message indicating that the relevant measurement unit 51 has been excluded from the conveying destination on the image display unit 82. The specimen is thus prevented from being measured by a reagent which is manufactured other than by the predetermined manufacturer and which reliability on the quality is not ensured.

In the above-described embodiment, conveyance devices 3, 3, 3 are configured in separate mechanisms, but is not limited thereto, and conveyance devices 3, 3, 3 may be configured in a single mechanism.

What is claimed is:

1. A specimen processing system comprising:
   a first measurement unit connected to a first reagent container and configured to measure a specimen for a predetermined measurement item by using a first reagent in the first reagent container;
   a second measurement unit connected to a second reagent container and configured to measure a specimen for the predetermined measurement item by using a second reagent in the second reagent container, wherein the first reagent and the second reagent are of same type;
   a conveyance mechanism configured to convey a specimen to at least one of the first and second measurement units; and
   a control system configured to:
      acquire first life information related to life of the first reagent and second life information related to life of the second reagent;
      determine a conveying destination of the specimen from among at least the first and second measurement units based on the acquired first and second life information; and
      control the conveyance mechanism to convey the specimen based on the determined conveying destination.

2. The specimen processing system according to claim 1, wherein
   the first life information includes first expiration date information related to a first expiration date of the reagent in the first reagent container; and
   the second life information includes second expiration date information related to a second expiration date of the reagent in the second reagent container.

3. The specimen processing system according to claim 2, wherein the control system is configured to determine the conveying destination to preferentially convey a specimen to one of the first and second measurement units which is connected to a reagent container storing a reagent for which a period until an expiration date is shorter than a predetermined period.

4. The specimen processing system according to claim 2, wherein the control system is configured to:
   compare the first and second expiration dates, and
   determine the conveying destination to preferentially convey a specimen to one of the first and second measurement units which is connected to a reagent container storing a reagent for which a period until an expiration date is the shortest.

5. The specimen processing system according to claim 1, wherein
   the first life information includes first manufacturing time information related to a first manufacturing time of the reagent in the first reagent container; and
   the second life information includes second manufacturing time information related to a second manufacturing time of the reagent in the second reagent container.

6. The specimen processing system according to claim 1, wherein the control system is configured to determine the conveying destination based on time information related to a time of determining the conveying destination and the first and second life information.

7. The specimen processing system according to claim 1, wherein the control system is configured to:
   set a conveyance mode of either a first conveyance mode of determining the conveying destination based on the first and second reagent information or a second conveyance mode of determining the conveying destination without based on the first and second reagent information;
   determine the conveying destination based on the first and second reagent information when the first conveyance mode has been set; and
   determine the conveying destination without based on the first and second reagent information when the second conveyance mode has been set.

8. The specimen processing system according to claim 1, wherein the control system is configured to:
   set a priority related to conveyance of specimens; and
   determine the conveying destination of the specimen based on the first and second reagent information and the priority set.

9. The specimen processing system according to claim 1, wherein
   the first reagent information includes first lot information of the reagent in the first reagent container;
   the second reagent information includes second lot information of the reagent in the second reagent container; and
   the control system is configured to determine the conveying destination based on the first and second lot information.

10. The specimen processing system according to claim 9, wherein the control system is configured to:
    acquire first manufacturer information related to a manufacturer of the reagent based on the first lot information;
    acquire second manufacturer information related to a manufacturer of the reagent based on the second lot information; and
    determine the conveying destination of the specimen based on the first and second manufacturer information.

11. The specimen processing system according to claim 1, wherein
    the control system includes a computer configured to determine the conveying destination of the specimen based on the acquired first and second reagent information and a conveyance controller configured to control the conveyance mechanism to convey the specimen based on the determined conveying destination; and the conveyance mechanism and the conveyance controller are included in a conveyance device.

12. The specimen processing system according to claim 1, wherein the first and second reagent containers include first and second identifiers recording the first and second reagent information, wherein the specimen processing system, further comprises a reagent information acquirer including a reading device for reading the first and second reagent information from the first and second identifiers.

13. The specimen processing system according to claim 1, wherein the first and second measurement units includes a blood cell analyzer for analyzing blood cells contained in a specimen.

14. A specimen conveyance method by a specimen processing system including first and second measurement units and a conveyance mechanism for conveying a specimen to at least one of the first and second measurement units, the method comprising:

acquiring i) first life information related to life of a first reagent stored in a first reagent container that is connected to the first measurement unit, the first measurement unit being configured to measure a specimen for a predetermined measurement item by using the first reagent in the first reagent container, and ii) second life information related to life of a second reagent stored in a second reagent container that is connected to the second measurement unit, the second measurement unit being configured to measure a specimen for the predetermined measurement item by using the second reagent in the second reagent container, wherein the first reagent and the second reagent are of same type;

determining a conveying destination of the specimen from among at least the first and second measurement units based on the acquired first and second life information; and conveying the specimen based on the determined conveying destination.

15. The conveyance method according to claim 14, wherein the acquiring is executed when a necessity to replace the reagent arises.

* * * * *